(12) United States Patent
Iwata et al.

(10) Patent No.: US 10,343,352 B2
(45) Date of Patent: Jul. 9, 2019

(54) FIBER-REINFORCED RESIN MATERIAL, MOLDED ARTICLE, METHOD AND DEVICE FOR MANUFACTURING FIBER-REINFORCED RESIN MATERIAL, AND FIBER BUNDLE GROUP INSPECTION DEVICE

(71) Applicant: Mitsubishi Chemical Corporation, Chiyoda-ku (JP)

(72) Inventors: Hiroshi Iwata, Tokyo (JP); Nobuyuki Yamamoto, Tokyo (JP); Hajime Okutsu, Tokyo (JP); Ryuichi Ishikawa, Tokyo (JP); Koichi Akiyama, Tokyo (JP); Takayuki Kobayashi, Tokyo (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 15/738,380

(22) PCT Filed: Jun. 24, 2016

(86) PCT No.: PCT/JP2016/068862
§ 371 (c)(1),
(2) Date: Dec. 20, 2017

(87) PCT Pub. No.: WO2016/208731
PCT Pub. Date: Dec. 29, 2016

(65) Prior Publication Data
US 2018/0162070 A1 Jun. 14, 2018

(30) Foreign Application Priority Data

Jun. 24, 2015 (JP) .................................. 2015-126814
Aug. 14, 2015 (JP) .................................. 2015-160158
Dec. 24, 2015 (JP) .................................. 2015-252244

(51) Int. Cl.
*C08J 5/04* (2006.01)
*B29B 11/16* (2006.01)
(Continued)

(52) U.S. Cl.
CPC .............. *B29C 70/12* (2013.01); *B29B 11/16* (2013.01); *B29B 15/08* (2013.01); *B29B 15/122* (2013.01);
(Continued)

(58) Field of Classification Search
CPC ....... B29B 11/16; B29B 15/08; B29B 15/122; B29C 70/12; B29C 70/06; C08J 2300/24;
(Continued)

(56) References Cited

U.S. PATENT DOCUMENTS 3,956,055 A  5/1976 Duft et al.
4,339,490 A * 7/1982 Yoshioka ................ B29C 70/00
428/213

(Continued)

FOREIGN PATENT DOCUMENTS

EP  0 025 689 A1  3/1981
EP  2 103 927 A2  9/2009
(Continued)

OTHER PUBLICATIONS

"Fibre-reinforced plastics composites—Determination of Flexural properties", K7017 Sen'i Kyoka Plastic—Mage Tokusei no Motomekata, JIS Handbook 26 Plastic I (Shiken), first edition, first print. Japanese Standards Association, Jan. 31, 2004, pp. 1060-1070.

(Continued)

*Primary Examiner* — Camie S Thompson
(74) *Attorney, Agent, or Firm* — Oblon, McClelland, Maier & Neustadt, L.L.P.

(57) ABSTRACT

The purpose of the present invention is to provide a fiber-reinforced resin material having minimal directionality of (Continued)

strength as well as excellent productivity, a method and device for manufacturing a fiber-reinforced resin material whereby a molded article is obtained, and a device for inspecting a fiber bundle group. A method for manufacturing a sheet-shaped fiber-reinforced resin material in which a paste (P1) is impregnated between cut fiber bundles (CF), the method for manufacturing a fiber-reinforced resin material including a coating step applying a coating of a paste (P1) on a first sheet (S11) conveyed in a predetermined direction, a cutting step for cutting a long fiber bundle (CF) using a cutter (113A), a scattering step for dispersing the cut fiber bundles (CF) and scattering the cut fiber bundles (CF) on the paste (P1), and an impregnation step for pressing a fiber bundle group (F1) and the paste (P1) on the first sheet (S11) and impregnating the paste (P1) between the fiber bundles (CF).

4 Claims, 17 Drawing Sheets

(51) Int. Cl.
| | |
|---|---|
| *B29B 15/08* | (2006.01) |
| *B29C 43/48* | (2006.01) |
| *B29C 43/58* | (2006.01) |
| *B29C 70/12* | (2006.01) |
| *B29B 15/12* | (2006.01) |
| *G01N 23/00* | (2006.01) |
| *G01N 21/84* | (2006.01) |

(52) U.S. Cl.
CPC .............. *B29C 43/48* (2013.01); *B29C 43/58* (2013.01); *C08J 5/042* (2013.01); *C08J 5/043* (2013.01); *G01N 21/84* (2013.01); *G01N 23/00* (2013.01); *C08J 2300/24* (2013.01); *G01N 2021/845* (2013.01); *G01N 2021/8416* (2013.01); *G01N 2021/8444* (2013.01)

(58) Field of Classification Search
CPC ..... C08J 5/042; C08J 5/043; C08J 5/24; C08J 2363/00; D06M 15/55; D06M 15/564
USPC ................................ 428/297.4, 299.1, 299.4
See application file for complete search history.

(56) References Cited

U.S. PATENT DOCUMENTS

| | | |
|---|---|---|
| 2006/0255300 A1 | 11/2006 | Shakespeare |
| 2009/0104418 A1 | 4/2009 | Ohki et al. |
| 2015/0212008 A1 | 7/2015 | Sasamoto et al. |
| 2015/0353713 A1 | 12/2015 | Miyoshi et al. |
| 2018/0245246 A1* | 8/2018 | Sinmen ...................... C08J 5/24 |

FOREIGN PATENT DOCUMENTS

| | | |
|---|---|---|
| JP | 57-039272 A | 3/1982 |
| JP | 09-094826 A | 4/1997 |
| JP | 2000-017557 A | 1/2000 |
| JP | 2007-187545 A | 7/2007 |
| JP | 2008-541088 A | 11/2008 |
| JP | 2010-076249 A | 4/2010 |
| JP | 2010-085166 A | 4/2010 |
| JP | 2012-162835 | 8/2012 |
| JP | 2014-035183 A | 2/2014 |
| JP | 2015-054480 A | 3/2015 |
| WO | WO 99/67625 A1 | 12/1999 |
| WO | 2006/124315 A1 | 11/2006 |
| WO | 2007/020910 A1 | 2/2007 |
| WO | 2014/129497 A1 | 8/2014 |
| WO | 2015/060299 A1 | 4/2015 |

OTHER PUBLICATIONS

International Search Report dated Aug. 30, 2016 in PCT/JP2016/068862, filed on Jun. 24, 2016.
Notice of Reasons for Revocation dated Jan. 7, 2019, in Japanese Application No. 2016-546859 (with English-language Translation).
Fiber encyclopedia, Maruzen Co., Ltd., issued on Mar. 25, 2002, pp. 170-177, (machine translation (related part only).
Manufacture and application of non-woven fabrics, CMC, The first impression of original publication Jun. 30, 1989, issued the first impression of popular edition Apr. 30, 2000, pp. 48-69. Machine translation (related part only).
State-of-the-art carbon fiber, CMC Publishing Ltd., the first impression of the first edition issued on Jan. 31, 2007, the first impression if the popular edition issued on Apr. 2013, pp. 20-21.
Office Acton dated May 21, 2019, in European Application No. EP16814500.1.
Written Opinion dated May 22, 2019, in JP 2016-546859 with Machine translation.
Decision of Opposition issued on May 22, 2019, in Japanese Patent No. 2016-546859 with Machine translation.

* cited by examiner

MD ⟶

MD ⟶

FIBER-REINFORCED RESIN MATERIAL, MOLDED ARTICLE, METHOD AND DEVICE FOR MANUFACTURING FIBER-REINFORCED RESIN MATERIAL, AND FIBER BUNDLE GROUP INSPECTION DEVICE

TECHNICAL FIELD

The present invention relates to a fiber-reinforced resin material, a molded article, a method and device for manufacturing a fiber-reinforced resin material, and a fiber bundle group inspection device.

This application is based upon and claims the benefit of priority from Japanese Patent Application No. 2015-126814 filed on Jun. 24, 2015, Japanese Patent Application No. 2015-160158 filed on Aug. 14, 2015, and Japanese Patent Application No. 2015-252244 filed on Dec. 24, 2015 in the Japanese Patent Office, the entire contents of which are hereby incorporated by reference.

BACKGROUND ART

SMC (Sheet Molding Compound) and stampable sheets are known as molding materials which are excellent in mechanical properties of molded articles and suitable for forming complex shapes such as three-dimensional shapes. The SMC is a sheet-shaped fiber-reinforced resin material obtained, for example, by impregnating a thermosetting resin such as an unsaturated polyester resin between fiber bundles obtained by cutting reinforced fibers such as glass fibers and carbon fibers. In addition the stampable sheet is a sheet-shaped fiber-reinforced resin material obtained, for example, by impregnating a thermoplastic resin into the above-described cut fiber bundle.

The SMC is an intermediate material for obtaining molded articles. When molding the SMC compressing (pressing) the SMC with heating using a mold is used. At this time, the fiber bundle and the thermosetting resin are filled into the cavity of the mold while flowing together, and after that, the thermosetting resin is cured. Therefore, by using the SMC it is possible to obtain molded articles of various shapes such as those having partially different thicknesses, those having ribs bosses, or the like. In addition, molded articles of the stampable sheet can be obtained by heating up to the melting point or more of a thermoplastic resin by an infrared heater or the like and cooling and pressing with a mold at a predetermined temperature.

In manufacturing the above-described SMC (fiber-reinforced resin material), a paste containing a thermosetting resin is applied on a sheet (carrier) to be conveyed, after that an elongated fiber bundle is cut into predetermined-length fiber bundles, and the predetermined-length fiber bundles are scattered on the paste (refer to, for example, Patent Literature 1).

However, according to the manufacturing method in the related art, the directions of the fiber bundles scattered on the paste tend to be aligned in a certain direction, and thus, directionality may occur in the strength of the manufactured SMC. Specifically, the fiber bundles that are cut by the cutting machine and dropped tend to collapse in the conveying direction of the sheet when landing on the conveyed sheet and tend to be aligned in the direction along the conveying direction of the sheet. In addition, as the length of the cut fiber bundles becomes longer or the conveying speed of the sheet becomes faster, this tendency appears more remarkably.

Therefore, in the SMC obtained by the manufacturing method in the related art, the strength thereof is increased in the conveying direction (longitudinal direction) of the sheet, and the directionality easily occurs such that the strength thereof becomes weaker in the direction (width direction) perpendicular to the conveying direction of the sheet. Therefore, in manufacturing the SMC, it is necessary to allow the directions of the fiber bundles scattered on the paste to be irregular (random) so that no directionality occurs in the strength of the SMC as described above. For example, although the directionality of this strength can be reduced by decreasing the conveying speed of the sheet, in this case, the productivity of the SMC is deteriorated. The same description is also applied to the case of the stampable sheet.

As a measure for allowing the orientations of the fiber bundles to be irregular, in the following Patent Literature 1, a method of uniformly dispersing the fiber bundles without directionality by tapping fiber bundles that are cut by a cutting machine and dropped with a rotating drum has been disclosed. However, when this method is used, fluff (fiber scrap) is generated from the fiber bundles tapped with the rotating drum. In particular, since the fiber bundles are loosened the more the rotation speed of the rotating drum is increased, the more fluff occurs. In addition, a drive source for rotationally driving the rotating drum is required.

CITATION LIST

Patent Literature

Patent Literature 1: JP 2000-17557 A

SUMMARY OF THE INVENTION

Problem to be Solved by the Invention

The invention has been proposed in view of such circumstances in the related art, and an object of the invention is to provide a fiber-reinforced resin material and a molded article which are less oriented in strength and superior in productivity. Another object of the invention is to provide a method and device for manufacturing a fiber-reinforced resin material capable of uniformly dispersing the cut fiber bundles without directionality when manufacturing a sheet-shaped fiber-reinforced resin material impregnated with a thermosetting resin or a thermoplastic resin between cut fiber bundles and a fiber bundle group inspection device which can be used for stably and continuously manufacturing the fiber-reinforced resin material as described above.

Means for Solving Problem

In order to achieve the above object, the invention provides the following means.

[1] A sheet-shaped fiber-reinforced resin material impregnated with a resin between dispersed fiber bundles, in which a diffracted X-ray at a diffraction angle $2\theta$ of 25.4° is detected by an X-ray diffraction method, and a roughness $\beta$ obtained by the following Mathematical Formulas (1) to (3) is in a range of 0.5 to 4.5.

[Mathematical Formula 1]

$$\beta = \int_0^{360} |f(\phi)| d\phi \times \frac{1}{360} = \left( \sum_{i=2}^{N} (|f(\phi_i)| + |f(\phi_{i-1})|) \times d\phi \times \frac{1}{2} \right) \times \frac{1}{360} \quad (1)$$

In the above Mathematical Formula, $f(\phi_i)$ is a luminance obtained by subtracting an average luminance from a luminance ($I(\phi_i)$) of an i-th rotation angle (d) in X-ray diffraction measurement represented by the following Mathematical Formula (2), and $d\phi$ is a step width of the X-ray diffraction measurement. $I(\phi_i)$ is normalized so that an integration strength represented by the following Mathematical Formula (3) becomes 10000.

[Mathematical Formula 2]

$$f(\phi_i) = I(\phi_i) - \frac{\sum_{i=1}^{N} I(\phi_i)}{N} \quad (2)$$

$$\int_0^{360} I(\phi) d\phi = \sum_{i=2}^{N} (I(\phi_i) + I(\phi_{i-1})) \times d\phi \times \frac{1}{2} = 10000 \quad (3)$$

[2] A sheet-shaped fiber-reinforced resin material impregnated with a resin between dispersed fiber bundles.

in which, when a longitudinal direction of the fiber-reinforced resin material is defined as a 0° direction and a width direction is defined as a 90° direction, a diffracted X-ray at a diffraction angle 2θ of 25.4° is detected by an X-ray diffraction method, and a sum of an average value and a standard deviation of a degree of crystal orientation $f_a$ of the fiber bundle based on the 0° direction obtained by the following Mathematical Formulas (4) to (6) is in a range of 0.05 to 0.13.

[Mathematical Formula 3]

$$f_a = 2a - 1 \quad (4)$$

$$a = \frac{\sum_{i=1}^{N} I(\phi_i)\cos^2 \phi_i}{\sum_{i=1}^{N} I(\phi_i)} \quad (5)$$

$$\int_0^{360} I(\phi) d\phi = \sum_{i=2}^{N} (I(\phi_i) + I(\phi_{i-1})) \times d\phi \times \frac{1}{2} = 10000 \quad (6)$$

In Mathematical Formula (4), "a" is an orientation coefficient represented by Mathematical Formula (5). $I(\phi_i)$ is a luminance at an i-th rotation angle ($\phi_i$) in X-ray diffraction measurement and is normalized so that an integration strength represented by Mathematical Formula (6) becomes 10000.

The fiber-reinforced resin material according to [1] or [2], in which the resin is a thermosetting resin.

[4] A molded article of the fiber-reinforced resin material according to any one of [1] to [3].

in which, when a longitudinal direction of the molded article is defined as a 0° direction and a width direction is defined as a 90° direction.

a ratio (0° bending modulus of elasticity/90° bending modulus of elasticity) of flexural moduli [GPa] of the respective directions is in a range of 0.8 to 1.2, and coefficients of variation (CV) (CV of 0° bending modulus of elasticity and CV of 90° bending modulus of elasticity) [%] of the bending moduli of elasticity in the respective directions are all in a range of 5 to 15.

[5] A method for manufacturing a sheet-shaped fiber-reinforced resin material impregnated with a resin between cut fiber bundles, including:

a coating step of coating a first sheet conveyed in a predetermined direction with the resin:

a cutting step of cutting an elongated fiber bundle with a cutting machine, a scattering step of dispersing cut fiber bundles and scattering the fiber bundles on the resin; and an impregnating, step of pressing a scattered fiber bundle group and the resin on the first sheet to impregnate the resin between the fiber bundles.

[6] The method for manufacturing a fiber-reinforced resin material according to [5], in which the impregnating step is a step of overlaying a second sheet coated with the resin on a first sheet on which the fiber bundles have been dispersed, after that pressing the resin and the fiber bundle group interposed between the first sheet and the second sheet to impregnate the resin between the fiber bundles.

[7] The method for manufacturing a fiber-reinforced resin material according to [5] or [6] in which the coating step is a step of coating the first sheet with a paste containing a thermosetting resin.

[8] The method for manufacturing a fiber-reinforced resin material according to any one of [5] to [7], in which the scattering, step is a step of arranging a plurality of rods side by side under the cutting machine and dropping cut fiber bundles toward the plurality of rods to disperse the fiber bundles to scatter the fiber bundles on the resin.

[9] The method for manufacturing a fiber-reinforced resin material according to [8], in which rods extending in a conveying direction of the first sheet are used as the plurality of rods.

[10] The method for manufacturing a fiber-reinforced resin material according to any one of [5] to [9], further including an inspecting step of inspecting, a fiber orientation state of the fiber bundle group scattered on the resin.

[11] The method for manufacturing a fiber-reinforced resin material according to [10], in which the inspecting step includes:

an imaging step of separately irradiating the fiber bundle group with first light and second light obliquely from an upper side in directions intersecting with each other as viewed in a plan view and capturing a still image of an upper surface of the fiber bundle group at a state of being irradiated with the first light or the second light, and an orientation determining step of calculating a luminance difference or a luminance ratio between a luminance in the state of being irradiated with the first light and a luminance in the state of being irradiated with the second light and determining the fiber orientation state of the fiber bundle group on the basis of luminance information obtained from the still image captured in the imaging step.

[12] The method for manufacturing, a fiber-reinforced resin material according to [10] or [11], further including a control step of changing a condition of the scattering step on the basis of an inspection result of the inspecting step to control the fiber orientation state of the fiber bundle group.

[13] The method for manufacturing a fiber-reinforced resin material according to [12], in which, in the control step, the fiber orientation state of the fiber bundle group is controlled by changing a conveying speed of the first sheet on the basis of the inspection result of the inspecting step.

[14] The method for manufacturing a fiber-reinforced resin material according to [12] or [13], in which the scattering step is a step of using the plurality of rods, and in which, in the control step, the fiber orientation state of the fiber bundle group is controlled by changing an inclination angle of the plurality of rods with respect to a horizontal direction on the basis of the inspection result of the inspecting step.

[15] The method for manufacturing a fiber-reinforced resin material according to [12] or [14], in which the scattering step is a step using the plurality of rods, and in which, in the control step, the fiber orientation state of the fiber bundle group is controlled by changing a frequency of the plurality of rods on the basis of the inspection result of the inspecting step.

[16] A device for manufacturing a sheet-shaped fiber-reinforced resin material impregnated with a resin between cut fiber bundles, including:

a coating unit which coats a first sheet conveyed in a predetermined direction with the resin;

a cutting unit which cuts an elongated fiber bundle with a cutting machine a scattering unit which disperses cut fiber bundles and scatters the fiber bundles on the resin; and an impregnation unit which presses a scattered fiber bundle group and the resin on the first sheet to impregnate the resin between the fiber bundles.

[17] The device for manufacturing a fiber-reinforced resin material according to [16], in which the impregnation unit is an impregnation unit which overlays a second sheet coated with the resin on a first sheet on which the fiber bundles have been dispersed, after that, presses the resin and the fiber bundle group interposed between the first sheet and the second sheet to impregnate the resin between the fiber bundles.

[18] The device for manufacturing a fiber-reinforced resin material according to [16] or [17] in which the scattering unit is a scattering unit which arranges a plurality of rods side by side under the cutting machine and drops cut fiber bundles toward the plurality of rods to disperse the fiber bundles.

[19] The device for manufacturing a fiber-reinforced resin material according to [18], in which the plurality of rods are rods extending in a conveying direction of the first sheet.

[20] A fiber bundle group inspection device comprising:

a first light irradiation means and a second light irradiation means which irradiate a fiber bundle group configured with a plurality of fiber bundles scattered continuously on a belt-shaped resin running in one direction with light obliquely from an upper side in directions intersecting each other as viewed in a plan view, an imaging means which is provided above the fiber bundle group and captures a still image of an upper surface of the fiber bundle group in a state of being irradiated with light by the first light irradiation means or the second light irradiation means; and an orientation determination means which calculates a luminance difference or a luminance ratio between a luminance in the state of being irradiated with light by the first light irradiation means and a luminance in the state of being irradiated with light by the second light irradiation means on the basis of luminance information obtained from the still image captured by the imaging means and determines a fiber orientation state of the fiber bundle group.

Effect of the Invention

As described above, the fiber-reinforced resin material and the molded article according to the invention have small directionality of strength and excellent productivity and can be appropriately used particularly as an SMC. In addition, according to the method and device for manufacturing, a fiber-reinforced resin material according to the invention, it is possible to increase the proportion of the fiber bundles that collapse in directions different from the conveying direction of the first sheet among the fiber bundles that are cut by the cutting machine and scattered on the resin. Therefore, it is possible to uniformly disperse the fiber bundles without directionality while suppressing generation of fluff (fiber scraps) from the fiber bundle. As a result, it is possible to maintain the strength of the fiber-reinforced resin material to be manufactured more uniform in all directions. In addition, by using the fiber bundle group inspection device according to the invention, it is possible to manufacture a fiber-reinforced resin material while inspecting the fiber orientation state of the fiber bundle group on the production line, so that it is possible to maintain the strength of the fiber-reinforced resin material to be manufactured more stable and uniform in the direction.

MODE(S) FOR CARRYING OUT THE INVENTION

Figure 1:
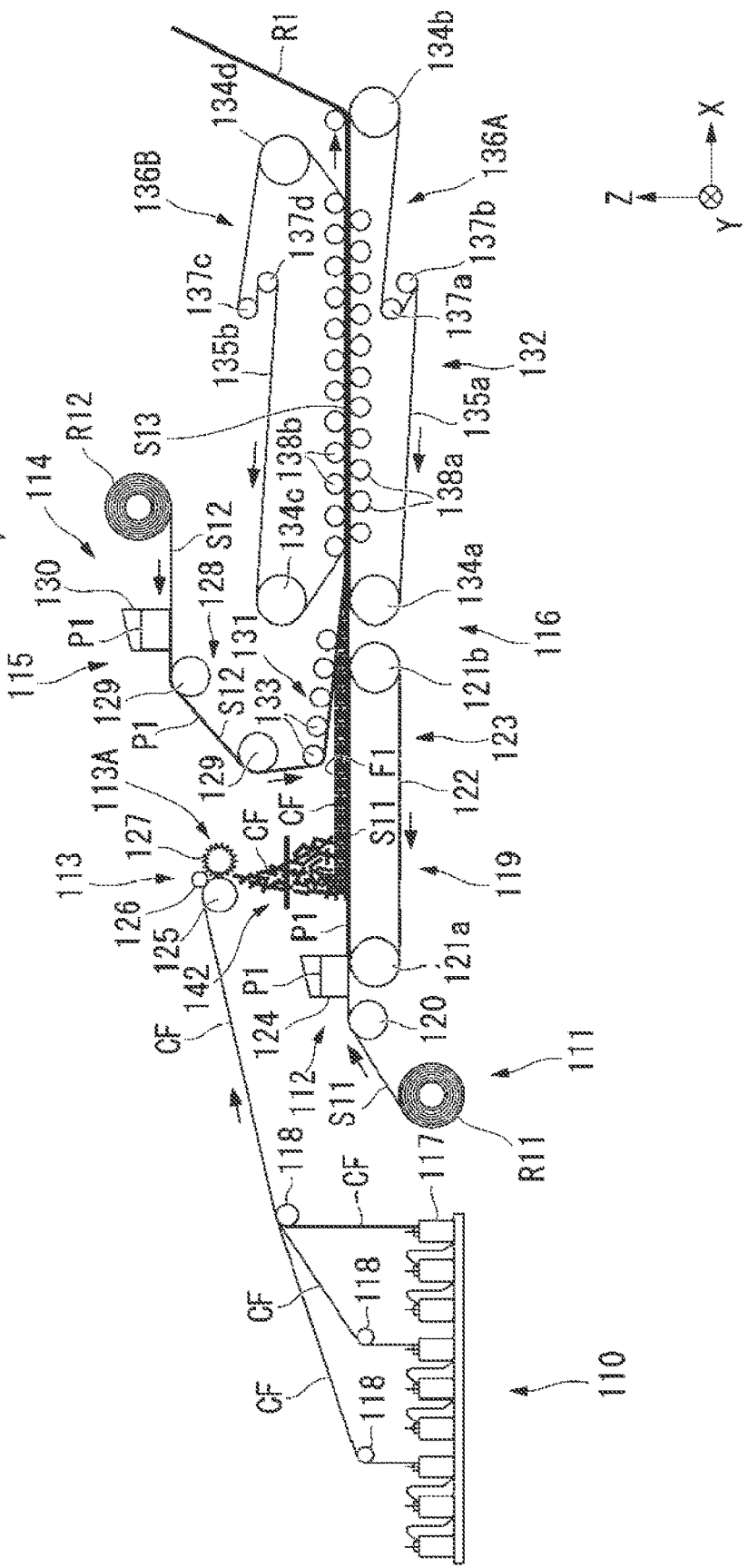
FIG. 1 is a side view illustrating a configuration of a device for manufacturing a fiber-reinforced resin material according to an embodiment of the invention.

Hereinafter, embodiments according to the invention will be described in detail with reference to the drawings.

In addition, in the drawings used in the following description, for the better understanding of features, there are cases where feature portions are enlarged for the sake of convenience, and the dimensional ratio of each component may not be the same as the actual one. In addition, materials, dimensions, and the like exemplified in the following description are merely examples, and the invention is not necessarily limited thereto, and appropriate changes and modifications are available within the scope without changing the spirit thereof.

The device and method for manufacturing a finer-reinforced resin material according to the invention are configured to manufacture a sheet-shaped fiber-reinforced resin material impregnated with a resin between cut filler bundles. The fiber-reinforced resin material obtained in the invention can be appropriately used as an SMC or a stampable sheet.

A fiber bundle is a bundle of a plurality of reinforced fibers. The reinforced fiber is preferably a carbon fiber. In addition, the reinforced fibers are not limited to carbon fibers, and reinforced fibers other than carbon fibers such as glass fibers may be used.

As a resin, a thermosetting resin or a thermoplastic resin may be used. As a resin, only a thermosetting; resin may be used, or only a thermoplastic resin may be used, and both a thermosetting resin and a thermoplastic resin may be used.

In the case where the fiber-reinforced resin material according to the embodiment is used as an SMC, a thermosetting resin is preferable as the resin. In the case where the fiber-reinforced resin material according to the embodiment is used as a stampable sheet, a thermoplastic resin is preferable as the resin.

As the thermosetting, resin, there may be exemplified an unsaturated polyester resin, an epoxy resin, a vinyl ester resin, a phenol resin, an epoxy acrylate resin, a urethane acrylate resin, a phenoxy resin, an alkyd resin, a urethane resin, a maleimide resin, a cyanate resin, and the like. As the thermosetting resin, one type may be used alone, or two or more types may be used in combination.

As the thermoplastic resin, there may be exemplified a polyolefin resin, a polyamide resin, a polyester resin, a polyphenylene sulfide resin, a polyether ketone resin, a polyether sulfone resin, an aromatic polyamide resin, and the like. As the thermoplastic resin, one type may be used alone, or two or more types may be used in combination.

First Embodiment

Hereinafter, a first embodiment of the invention will be described.

(Device for Manufacturing Fiber-Reinforced Resin Material)

As an example of a device for manufacturing a fiber-reinforced resin material according to the first embodiment, a case of manufacturing, a sheet-shaped SMC impregnated with a paste containing a thermosetting resin such as an unsaturated polyester resin between fiber bundles obtained by cutting an elongated fiber bundle made of carbon fibers will be described.

FIG. 1 is a side view illustrating a configuration or a device for manufacturing, a fiber-reinforced resin material according to the embodiment. In addition, in the following description, an XYZ rectangular coordinate system is set, and a positional relationship of each member will be described with reference to the XYZ rectangular coordinate system.

As illustrated in FIG. 1, the device for manufacturing a fiber-reinforced resin material 11 according to the embodiment (hereinafter, simply referred to as the manufacturing device 11) is configured to include a fiber bundle supply unit 110, a first sheet supply unit 111, a first coating unit 112, a cutting unit 113, a scattering unit 142 a second sheet supply unit 114, a second coating unit 115, and an impregnation unit 116.

While drawing out fiber bundles CF configured with elongated carbon fibers from a plurality of bobbins 117, the fiber bundle supply unit 110 forms one fiber bundle CF through a plurality of guide rollers 118 and supplies the fiber bundle CF to the cutting unit 113.

The first sheet supply unit 111 supplies an elongated first sheet (carrier sheet) S11 unwound from the first raw fabric roll R11 toward the first coating unit 112. The manufacturing device 11 is configured to include a first conveying unit 119 that conveys the first sheet S11 in a predetermined direction X axis direction) thereinafter, referred to as a conveying direction).

The first conveying unit 119 is configured to include a guide roller 120 and a conveyor 123 in which an endless belt 122 is hung between a pair of pulleys 121a and 121b. While rotating, the guide roller 120 guides the first sheet S11 supplied from the first sheet supply unit 111 toward the conveyor 123. While rotating the endless belt 122 by rotating the pair of pulleys 121a and 121b in the same direction, the conveyor 123 moves the first sheet S11 on the surface of the endless belt 122 in the +X axis direction (toward the right side m the horizontal direction).

The first coating unit 112 is located immediately above the one pulley 121a close to the guide roller 120 and is provided with a supply box 124 for supplying a paste P1 containing a thermosetting resin. The supply box 124 coats the surface of the first sheet S11 conveyed by the conveyor 123 with the paste P1 having a predetermined thickness from a slit (not shown) formed on the bottom surface thereof.

In addition, besides the thermosetting resin such as an unsaturated polyester resin, a paste mixed with a filler such as calcium carbonate, a low shrinkage reducing agent, a releasing agent, a curing initiator, a thickener, and the like may be used as the paste P1.

The cutting unit 113 is located at the downstream side (+X axis side) in the conveying direction with respect to the first coating unit 112 and cuts the fiber bundle CF supplied from the fiber bundle supply unit 110 by a cutting machine 113A and scatters the cut fiber bundles on the paste P1. The cutting machine 1134 is located above the first sheet S11 conveyed by the conveyor 123 and is configured to include a guide roller 125, a pinch roller 126, and a cutter roller 127.

While rotating, the guide roller 125 guides the fiber bundle CF supplied from the fiber bundle supply unit 110 downward. The pinch roller 126 rotates in a direction opposite to that of the guide roller 125 while interposing the fiber bundle CF with the guide roller 125, so that the fiber bundle CF is drawn out from the plurality of bobbins 117 in cooperation with the guide roller 125. While rotating, the cutter roller 127 cuts the fiber bundle CF so as to have a predetermined length. The cut fiber bundles CF are dropped from the portion between the guide roller 125 and the cutter roller 127 and are scattered on the paste P1 applied on the first sheet S11.

The second sheet supply unit 114 supplies an elongated second sheet (carrier sheet) S12 unwound from a second raw fabric roll R12 toward the second coating unit 115. The manufacturing device 11 is configured to include a second conveying unit 128 that conveys the second sheet S12 toward the impregnation unit 116.

The second conveying unit 128 is located above the first sheet S11 conveyed by the conveyor 123 and is configured to include a plurality of guide rollers 129. The second conveying unit 128 conveys the second sheet S12 supplied from the second sheet supply unit 114 toward the −X axis direction (toward the left side in the horizontal direction) in FIG. 1, and after that, the direction in which the second sheet S12 is conveyed by the plurality of rotating guide roller 129 is reversed from the lower side in the +X axis direction (toward the right side in the horizontal direction) in FIG. 1.

The second coating unit 115 is configured to include a supply box 130 that is located just above the second sheet S12 which is conveyed toward the −X axis direction (toward the left side in the horizontal direction) in FIG. 1 and supplies the paste P1. The supply box 130 coats the surface of the second sheet S12 with a paste P1 having a predetermined thickness from a slit (not shown) formed on the bottom surface thereof.

The impregnation unit 116 is located at the downstream side in the conveying direction with respect to the cutting unit 113 and is configured to include a bonding mechanism 131 and a pressing mechanism 132. The bonding mechanism 131 is located above the other pulley 121b of the conveyor 123 and is configured to include a plurality of hording rollers 133.

The plurality of bonding rollers 133 are arranged side by side in the conveying direction in the state of being in contact with the back surface of the second sheet S12 coated with the paste P1. In addition the plurality of bonding rollers 133 are arranged so that the second sheet S12 gradually approaches the first sheet S11.

In the bonding mechanism 131, the second sheet S12 is superimposed on the first sheet S11. In addition, the first sheet S11 and the second sheet S12 are conveyed to the pressing mechanism 132 side in the state where the sheets are bonded together while interposing the fiber bundle CF and the paste P1 therebetween. Hereinafter, the first sheet S11 and the second sheet S12 bonded together while interposing the fiber bundle CF and the paste P1 are referred to as a bonding sheet S13.

The pressing mechanism 132 is located at the downstream of the first conveying unit 119 (conveyor 123) and is configured to include a lower conveyor 136A in which an endless belt 135a is hung between a pair of pulleys 134a and 134b and an upper conveyor 136B in which an endless belt 135b is hung between a pair of pulleys 134c and 134d.

The lower conveyor 136A and the upper conveyor 136B are arranged to face each other in the state where the endless belts 135a and 135b abut each other. The pressing mechanism 132 revolves the endless belt 135a by rotating the pair of pulleys 134a and 134b of the lower conveyor 136A in the same direction. In addition, the pressing mechanism 132 revolves the endless belt 135b in the opposite direction at the same speed as that of the endless belt 135a by rotating the pair of pulleys 134c and 134d of the upper conveyor 136B in the same direction. Therefore, the bonding sheet S13 interposed between the endless belts 135a and 135b is conveyed in the +X axis direction (toward the right side in the horizontal direction) in FIG. 1.

On the lower conveyor 136A, a pair of tension pulleys 137a and 137b for adjusting the tension applied to the endless belt 135a are arranged. Similarly, on the upper conveyor 136B, a pair of tension pulleys 137c and 137d for adjusting the tension applied to the endless belt 135b are arranged. These tension pulleys 137a, 137b, 137c, and 137d are provided on the side opposite to the abutting portion of the endless belts 135a and 135b.

The pressing, mechanism 132 is configured to include a plurality of lower rollers 138a and a plurality of upper rollers 138b. The plurality of lower rollers 138a are arranged side by side in the conveying direction in the state of being in contact with the hack surface of the abutting portion of the endless belt 135a. Similarly, the plurality of upper rollers 138b are arranged side by side in the conveying direction in the state of being in contact with the hack surface of the abutting portion of the endless belt 135b. In addition, the plurality of lower rollers 138a and the plurality of upper rollers 138b are alternately arranged side by side in the conveying direction of the bonding sheet S13.

In the pressing mechanism 132, while the bonding sheet S13 passes between the endless belts 135a and 135b, the paste P1 and the fiber bundle CF interposed between the first sheet S11 and the second sheet S12 are pressed by the plurality of lower rollers 138a and the plurality of upper rollers 138b. At this time, the paste P1 is impregnated between the filler bundles CF from both sides interposing the fiber bundle CF.

Therefore, it is possible to obtain the SMC raw fabric R1 impregnated with the thermosetting resin between the fiber bundles CF. In addition, the SMC raw fabric R1 is finally shipped as a sheet-shaped SMC (fiber-reinforced resin material) by being cut to have a predetermined length. In addition, the first sheet S11 and the second sheet S12 are peeled from the SMC before SMC molding.

In the device for manufacturing a fiber-reinforced resin material according to the invention, as in this example, it is preferable that the impregnation unit may be an impregnation unit which impregnates a resin between the fiber bundles by overlaying the second sheet coated with the resin on the first sheet to which the fiber bundles have been scattered and, after that, pressing the resin and the fiber bundles interposed between the first sheet and the second sheet. Therefore, it possible to obtain a fiber-reinforced resin material excellent in mechanical properties sufficiently impregnated with a resin as compared with the impregnation unit in which the second sheet coated with the resin is not overlaid.

In addition, the impregnation unit may be an impregnation unit which impregnates the resin between the fiber bundles by pressing the resin and the fiber bundle group without further overlaying the second sheet coated with the resin on the first sheet on which the fiber bundles have been scattered.

Figure 2:
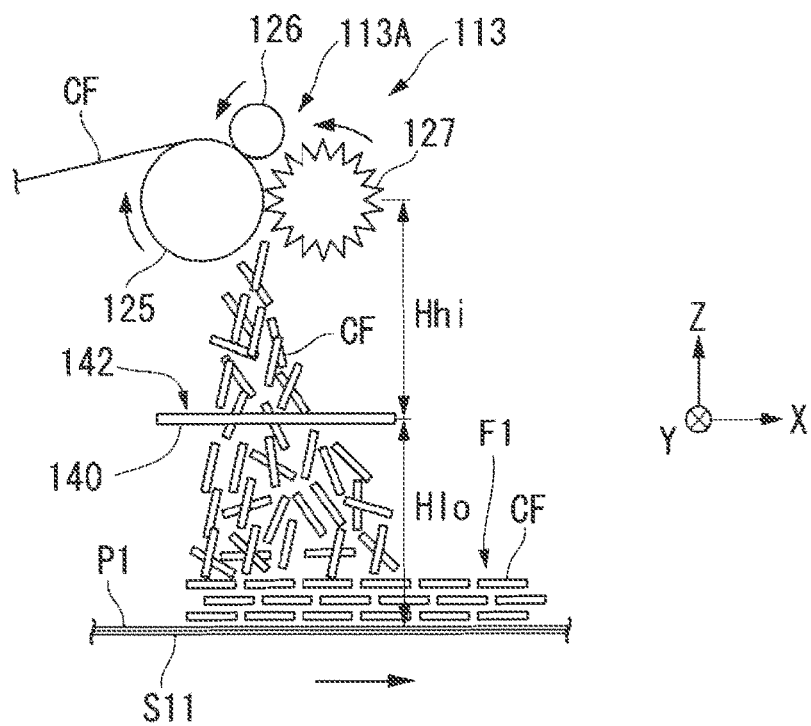
FIG. 2 is an enlarged side view illustrating a cutting unit of the device for manufacturing a fiber-reinforced resin material illustrated in FIG. 1.
Figure 3:
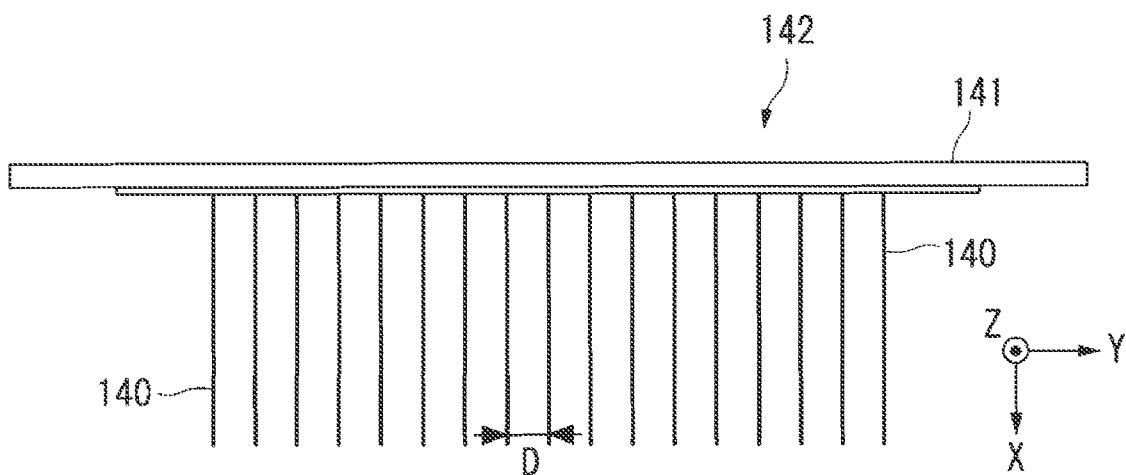
FIG. 3 is a plan view OF a plurality a rods arranged in the cutting unit illustrated in FIG. 2.

As illustrated in FIGS. 1 to 3, the manufacturing device 11 according to the embodiment is provided with a scattering unit 142 under the cutting machine 13A. The scattering unit 142 is configured to include a support rod 141 and a plurality of rods 140 extending in the conveying direction of the first sheet S11.

As illustrated in FIG. 3, the plurality of rods 140 are arranged in parallel to each other with an interval D therebetween in the width direction (Y axis direction) of the first sheet S11 so as not to overlay with each other as viewed in a plan view as illustrated in FIG. 3. Namely, the plurality of rods 140 are arranged in parallel to each other with an interval D therebetween in the width direction (Y axis direction) of the first sheet S11 as viewed in a plan view so that the longitudinal direction thereof is the longitudinal direction (X axis direction) of the first sheet S. In addition, each of the rods 140 is supported in a cantilever manner that each base end side (−X axis side) is attached to the support rod 141 extending in the width direction of the first seat S11.

Figure 4A:
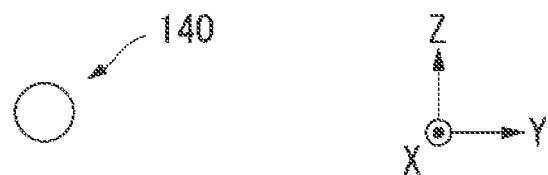
FIG. 4A is a cross-sectional view illustrating the cross-sectional shape of the rod illustrated in FIG. 3.
Figure 4B:
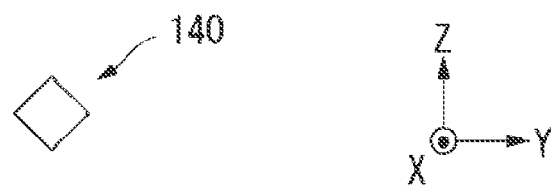
FIG. 4B is a cross-sectional view illustrating another example of the cross-sectional shape of the rod.
Figure 4C:
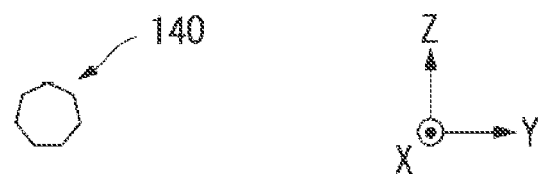
FIG. 4C is a cross-sectional view illustrating still another example of the cross-sectional shape of the rod.

In addition, each rod 140 has a circular cross-sectional shape as illustrated in FIG. 4A. The diameter of each rod 140 is in a range of about 0.1 to 10 mm. The cross-sectional shape of the rod 140 is not limited to a circle (including an ellipse) illustrated in FIG. 4A, but the cross-sectional shape may be appropriately modified to be a rhombus (a quadrangle) illustrated in FIG. 4B, a polygon (a heptagon in this example) illustrated in FIG. 4C, or the like.

As illustrated in FIG. 2, the plurality of rods 140 are arranged at the same height and parallel to the first sheet S11 when the cross section of the first sheet S11 is viewed. In addition, it is preferable that the plurality of rods 140 are arranged at positions separated by an interval (height) of at least 150 mm or more downward from the cutting machine 113A. On the other hand, it is preferable that the plurality of rods 140 are arranged at positions separated by an interval (height) Hlo of at least 200 mm or more upward from the first sheet S11.

In the manufacturing device 11 having the above-described configuration, among the fiber bundles CF that are cut by the cutting machine 113A and dropped, the fiber bundles CF that are in contact with the rods 140 of the scattering unit 142 tend to collapse in directions different from the conveying direction of the first sheet S11. Therefore, by using a simple method of arranging the plurality of rods 140 under the cutting machine 113A, while suppressing generation of fluff (fiber scraps) from the fiber bundles CF, the fiber bundles CF can be uniformly dispersed without directionality.

The device for manufacturing the fiber-reinforced resin material according to the invention is not limited to the manufacturing device 11 described above. For example, instead of the scattering unit 142 having the plurality of rods 140, a scattering unit having a gas diffuser for blowing a gas such as air to the fiber bundles CF which are cut and dropped may be installed. It is possible to uniformly disperse the fiber bundles CF without directionality by blowing a gas under a predetermined condition to the fiber bundles CF which are cut and dropped.

The device for manufacturing a fiber-reinforced resin material according to the invention may be a manufacturing device for manufacturing a fiber-reinforced resin material used for a stampable sheet using a thermoplastic resin instead of a thermosetting resin.

(Method for Manufacturing Fiber-Reinforced Resin Material)

Next, as a method for manufacturing the fiber-reinforced resin material according to the first embodiment, a method for manufacturing the SMC using the manufacturing device 11 will be described in detail. The method for manufacturing an SMC according to the embodiment includes the following coating step, cutting step, scattering step, and impregnating step.

Coating Step: The paste P1 is allowed to be applied on the first sheet S11 conveyed by the first conveying unit 119.

Cutting Step: An elongated fiber bundle CF is allowed to be cut with a cutting machine 113A.

Scattering Step: The cut fiber bundles CF are allowed to be dispersed and scattered on the paste P1 applied on the first sheet S11 by the scattering unit 142.

Impregnating Step: The paste P1 on the first sheet S11 and the scattered fiber bundle group F1 are allowed to be pressed to impregnate the paste P1 between the fiber bundles CF.

<Coating Step>

The first sheet supply unit 111 unwinds the elongated first sheet S11 from the first raw fabric roll R11 and supplies the unwound first sheet S11 to the first conveying unit 119, and the first coating unit 112 applies the paste P1 having a predetermined thickness. The first sheet S11 is conveyed by the first conveying unit 119, so that the paste P1 applied on the first sheet S11 is allowed to run. The thickness of the paste P1 applied on the surface of the first sheet S11 is not particularly limited.

<Cutting Step>

The elongated fiber bundle CF is drawn out from the plurality of bobbins 117 by the fiber bundle supply unit 110 and supplied to the cutting unit 113, and the fiber bundle CF is continuously cut with a predetermined length in the cutting machine 113A.

<Scattering Step>

The fiber bundles CF cut by the cutting machine 113A are dropped toward the plurality of rods 140 arranged side by side under the cutting, machine 113A, and the fiber bundles CF are dispersed by the rods 140 and scattered on the applied paste P1. Therefore, a sheet-shaped fiber bundle group F is formed on the applied paste P1.

In the embodiment, the plurality of rods 140 extending in the conveying direction of the first sheet S11 are arranged side by side wider the cutting machine 113A, so that the fiber bundles CF in contact with the rods 140 tend to collapse in directions different from the conveying direction of the first sheet S11.

Figure 5A:
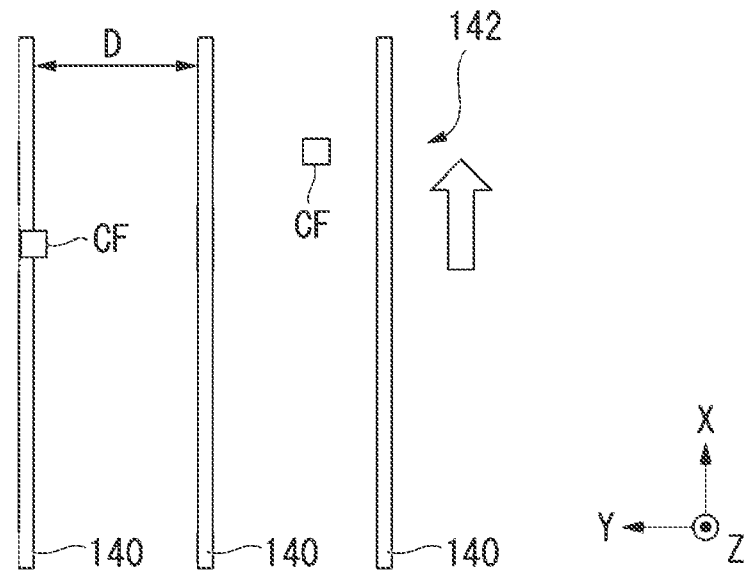
FIG. 5A is a plan view schematically illustrating a behavior of fiber bundles in contact with rods.
Figure 5B:
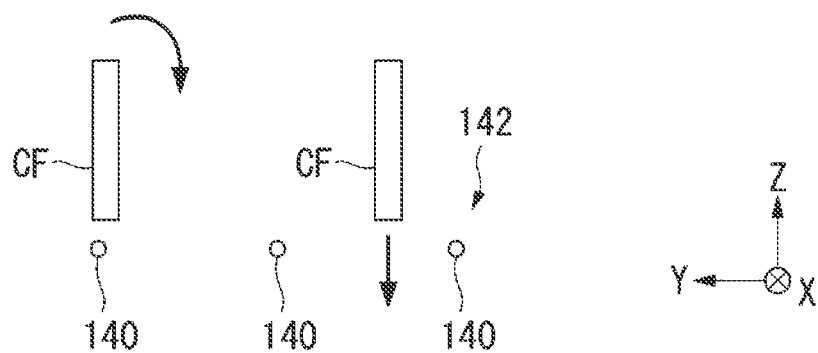
FIG. 5B is a front view schematically illustrating a behavior of fiber bundles in contact with the rods.
Figure 5C:
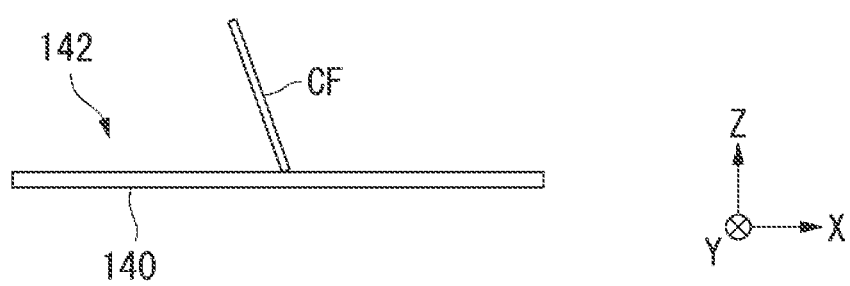
FIG. 5C is a side view schematically illustrating a behavior of fiber bundles in contact with the rods.

Herein, the behavior of the fiber bundles CF in contact with the rods 140 will be described with reference to FIGS. 5A to 5C. FIG. 5A is a plan view schematically illustrating the behavior of the fiber bundles CF in contact with the rods 140. FIG. 5B is a front view thereof, and FIG. 5C is a side view thereof.

The fiber bundles CF cut by the cutting machine 113A are naturally dropped downward (in the −Z axis direction). At this time, since each of the fiber bundles CF has a certain width (bundle width), after being in contact with the rods 140, the fiber bundles CF are dropped on the first sheet S11 while moving in the circulating direction of the rods 140.

In this case, the fiber bundles CF landed on the paste P1 of the first sheet S11 tend to collapse in the width direction (Y axis direction) of the first sheet S11. On the other hand, the fiber bundles CF landed on the paste P1 of the first sheet S11 without being in contact with the rods 140 tend to collapse in the conveying direction (X axis direction) of the first sheet S11 as described above. Therefore, it possible to allow the orientations of the fiber bundles CF collapsing on the paste P1 of the surface of the first sheet S11 to be irregular (random).

Therefore, according to the SMC manufacturing method according to the embodiment, by using a simple method of arranging the plurality of rods 140 under the cutting machine 113A, it is possible to suppress generation of fluff (fiber scraps) from the fiber bundles CF, and it is possible to uniformly disperse the fiber bundles CF without directionality. As a result, it is possible to maintain the strength of the manufactured SMC to be uniform in all directions.

In the invention, by setting the interval D between the adjacent rods 140 illustrated in FIG. 3 to be larger than the length of the fiber bundle CF dropped from the cutting machine 113A, it is possible to prevent the fiber bundles CF from being deposited between the rods 140.

However, if the interval D between the rods 140 is too large, the number of the fiber bundles CF that are in contact with the rods 140 is decreased, so that the above-described effect is weakened. On the other hand, if the interval D between the rods 140 is too narrow, the fiber bundles CF may be deposited between the rods 140 in a straddling state.

Therefore, in the invention, it is preferable that the interval D between the adjacent rods 140 as the first sheet S11 is viewed in plan is in a range of 0.9 to 1.6 times the average length of the fiber bundles CF cat by the cutting machine 113A. Therefore, it is possible to uniformly disperse the fiber bundles CF without directionality.

In addition, among the fiber bundles CF, there occurs the fiber bundles of which portion is joined without being cut during the cutting, the fiber bundles which are repeatedly cut to be shortened, or the like. For this reason, although irregularity occurs in the lengths of the cut fiber bundles CF, the average length of the fiber bundles CF described above can be obtained by excluding the fiber bundles having such exceptionally different lengths.

Figure 6:
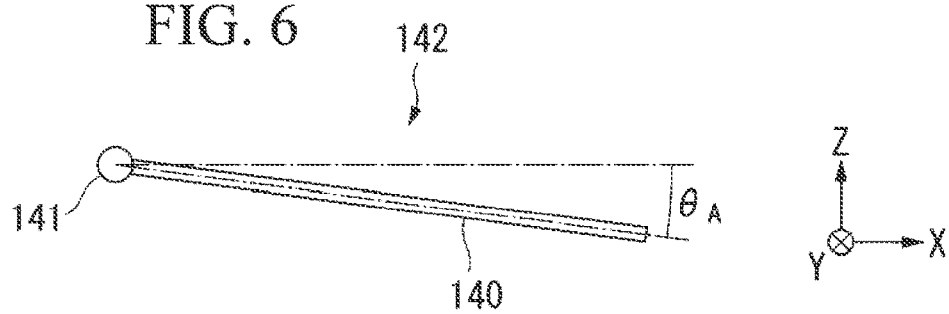
FIG. 6 is a side view illustrating a configuration where the rods are arranged in an inclined state.

In addition, in the invention, as illustrated in FIG. 6, the plurality of rods 140 may be inclined downward (in the −Z axis direction) in the conveying direction (+X axis direction) of the first sheet S11. Namely, the plurality of rods 140 may arranged in the state where the distal end side (+X axis side) is inclined downward (in the −Z axis direction) with respect to the base end side (−X axis side) attached to the support rods 141. In this case, it is preferable that the inclination angle of the plurality of rods 140 with respect to the plane parallel to the first sheet S11 is larger than 0° and equal to or smaller than 40°.

Therefore, it is possible to prevent the fiber bundle CF from being deposited between the rods 140 in a straddling state as described above, and it is possible to allow the fiber bundle CF to be surely dropped on the surface of the first sheet S11 in the inclination of the rods 140.

In addition, the invention is not limited to such a configuration, but a configuration where the plurality of rods 140 are inclined downward (in the −Z axis direction) in a direction opposite to the conveying direction of the first sheet S11 (−X axis direction) may be employed. In this case, the plurality of rods 140 may be arranged in the state where the base end side attached to the support rods 141 is on the +X axis side and the distal end side (−X axis side) is inclined downward (in the −Z axis direction).

Figure 7A:
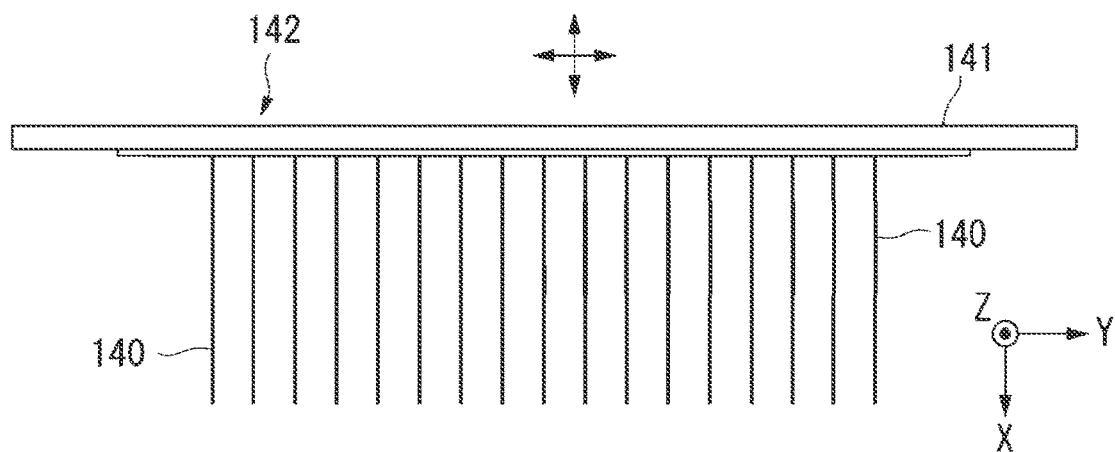
FIG. 7A is a plan view schematically illustrating an operation of vibrating the rods.
Figure 7B:
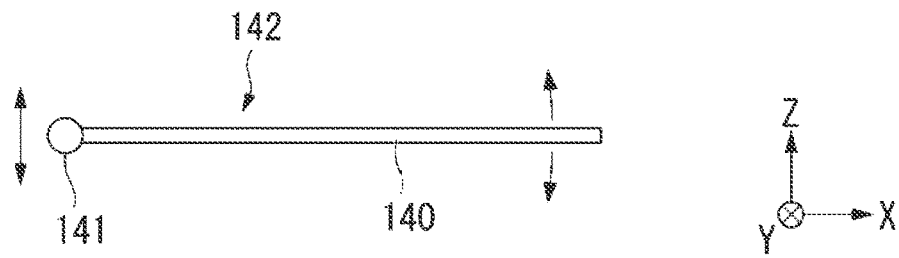
FIG. 7B is a side view schematically illustrating the operation of vibrating the rods.

In addition, in the invention, as illustrated by arrows in FIGS. 7A and 7B, the plurality of rods 140 may be configured to be vibrated. In addition, FIG. 7A is a plan view schematically illustrating the operation for explaining the operation of vibrating the plurality of rods 140, and FIG. 7B is a side view thereof.

In this case, the direction in which the plurality of rods 140 are vibrated may be any one of the longitudinal direction (X axis direction), the width direction (Y axis direction), and the height direction (Z axis direction). In addition, a configured may be employed where the plurality of rods 140 are vibrated in a plurality of directions. In addition, the plurality of rods 140 may be swung around the support rods 141.

Therefore, it is possible not only to prevent the fiber bundle CF from being deposited between the rods 140 in a straddling state as described above and hut also to more uniformly disperse the fiber bundles CF surely dropped on the surface of the first sheet S11 without directionality.

In addition, the invention is not necessarily to those of the above embodiment, and various modifications are available within the scope without deviating from the spirit of the invention.

Figure 8:
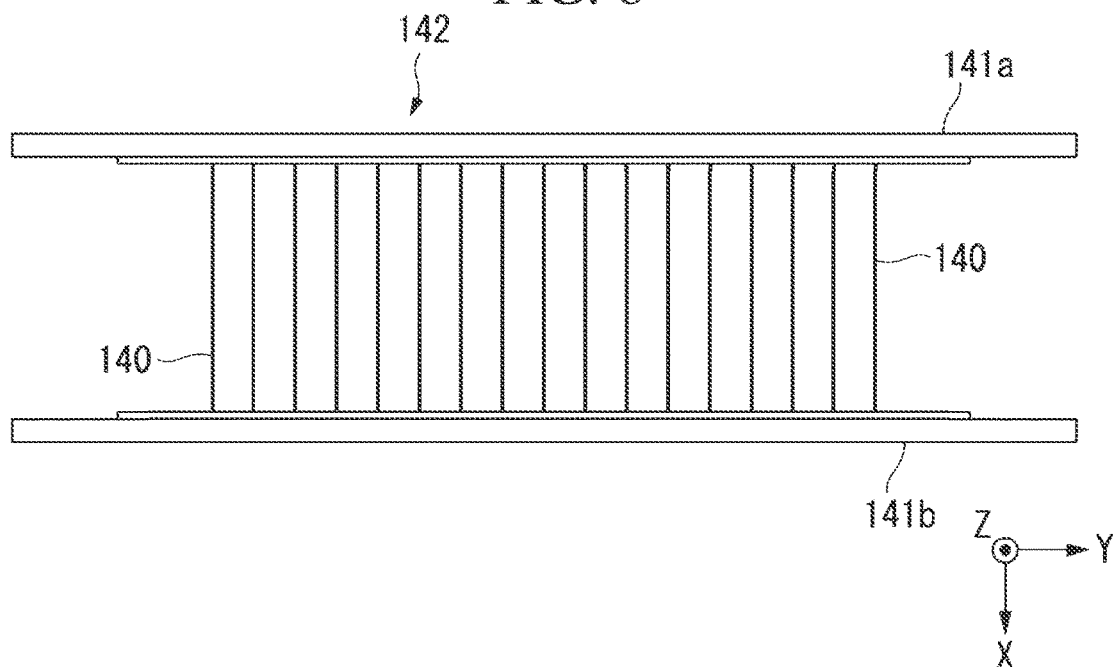
FIG. 8 is a plan view illustrating, a structure where each rod is supported at both ends.

Specifically, the plurality of rods 140 are not limited to the above-described configuration where the plurality of rods are supported in a cantilever manner, but as illustrated in FIG. 8, for example, the plurality of rods 140 may be configured to be supported between a pair of support rods 141a and, 141b extending in the width direction of the first sheet S11 in a both-end support manner where both ends thereof are attached to the support rods 141a and 141b.

Figure 9:
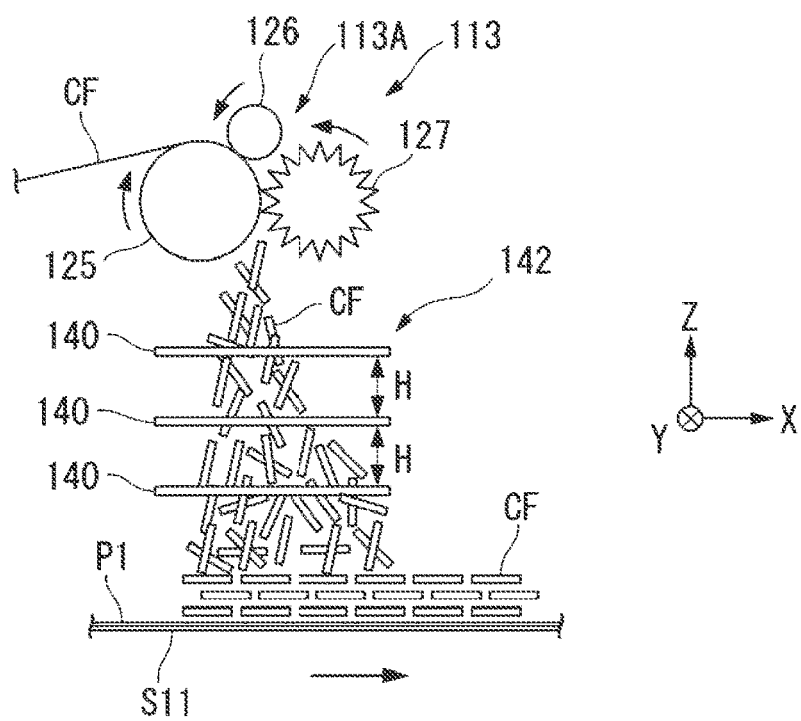
FIG. 9 is a side view illustrating a configuration where rods are arranged with spaces in a height direction.

In addition, as illustrated in FIG. 9, in addition to the configuration where the plurality of rods 140 are arranged with an interval D therebetween in the width direction (Y axis direction) of the first sheet S11 as described above, the plurality of rods may be configured to be arranged with an interval H therebetween in the height direction (Z axis direction).

The plurality of rods 140 may be arranged in multiple stages in the height direction (Z axis direction). In this case, it is preferable that the interval H in the height direction of the plurality of rods 140 is larger than the length of the fiber bundle CF dropped from the cutting machine 113A.

In addition, the plurality of rods 140 are configured to extend in the conveying direction (X axis direction) of the first sheet S11, but the configuration is not limited to the case where the rods 140 may be arranged in parallel to the conveying direction (X axis direction) of the first sheet S11, and the rods 140 may be arranged obliquely with respect to the conveying direction (X axis direction) of the first sheet S11.

In addition, as a method of dispersing the fiber bundles, as described in international Publication No. 2014/017612, the fiber bundles can be supplied while sucking from the bottom of the net. However, in order to apply the fiber bundles to the manufacturing of a fiber-reinforced resin material that needs the fiber bundles to be dropped on the resin, further contrivance is necessary. There are various methods of uniformly dispersing the fiber bundles without directionality by lowering the conveying speed of the sheet, but in that case, it is necessary to sacrifice productivity to some extent.

<Impregnating Step>

The second sheet supply unit 114 unwinds the elongated second sheet S12 from the second raw fabric roll R12 and supplies the unwound second sheet S12 to the second conveying unit 128. The paste P1 having a predetermined thickness is applied on the second sheet S12 by the second coating unit 115. The thickness of the paste P1 applied on the surface of the second sheet S12 is not particularly limited.

The paste P1 applied thereon is allowed to move by conveying the second sheet S12, and in the impregnation unit 116, the second sheet S12 is bonded on the sheet-shaped fiber bundle group F1 by the bonding mechanism 131. Then, the pressing mechanism 132 presses the sheet-shaped fiber bundle group F1 and the paste P1 to impregnate the paste P1 between the fiber bundles CF of the fiber bundle group F1. Therefore the raw fabric R1 in which the fiber-reinforced resin material is interposed between the first sheet S11 and the second sheet S12 is obtained.

As in this example, it is preferable that, the impregnating step in the manufacturing method according to the invention is a step of impregnating a resin between the fiber bundles by overlaying the second sheet coated with the resin on the first sheet on which the fiber bundles are scattered and, after that, by pressing the resin and the fiber bundle group interposed between the first sheet and the second sheet. Therefore, it possible to obtain a fiber-reinforced resin material excellent in mechanical properties sufficiently impregnated with a resin as compared with the impregnating step in which the second sheet coated with the resin is not overlaid.

In addition, the impregnating step may be an impregnating step of impregnating a resin between the fiber bundles by pressing the resin and the fiber bundle group without further overlaying the second sheet coated with the resin on the first sheet on which the fiber bundles are scattered.

As described above, in the SMC manufacturing method according to the embodiment, it is possible to uniformly disperse the cut fiber bundles CF without directionality by using the above-described simple method. As a result, it is possible to maintain the strength of the manufactured SMC to be uniform in all directions, and it is also possible to improve the productivity of the SMC.

In addition, the method for manufacturing a fiber-reinforced resin material according to the invention is not limited to a method using the manufacturing device 11. For example, instead of the scattering unit 142, a method having a step of dispersing, and scattering the fiber bundles by blowing a gas such as air to the fiber bundles which are cut and dropped may be employed. It is possible to uniformly disperse the fiber bundles CF without directionality by blowing a gas under a predetermined condition to the fiber bundles CF which are cut and dropped.

The method for manufacturing, a fiber-reinforced resin material according to the invention may be a method for manufacturing a fiber-reinforced resin material to be used for a stampable sheet by using a thermoplastic resin instead of a thermosetting resin.

Second Embodiment

In the device and the method for manufacturing a fiber-reinforced resin material according to the invention, it is preferable to inspect the fiber orientation state of the fiber bundle group formed by scattering the cut fiber bundles on the resin before impregnating the resin.

In order to obtain a molded article excellent in isotropic mechanical properties by using a fiber-reinforced resin material such as SMC, it is important that the fiber orientation of the fiber bundle in the fiber-reinforced resin material has no bias, but it is difficult to inspect the fiber orientation state of each fiber bundle in the fiber-reinforced resin material impregnated with the resin after the production. However, by checking the fiber orientation state of the fiber bundle group before impregnating the resin, it is possible to determine the fiber orientation state of the fiber bundle in the fiber-reinforced resin material. The fiber orientation state of the fiber bundle group can be inspected, for example, by using the fiber bundle group inspection device according to the invention which will be described later.

(Fiber Bundle Group Inspection Device)

The fiber bundle group inspection device according to the invention is a device for inspecting the fiber orientation state of the fiber bundle in a sheet-shaped fiber bundle group configured with the plurality of fiber bundles continuously scattered on a belt-shaped resin running in one direction. By using the fiber bundle group inspection device according to the invention, it is possible to inspect the fiber orientation state of the fiber bundle in the fiber bundle group on the production line of the fiber-reinforced resin material.

The fiber bundle group inspection device according to the invention is configured to include a first light irradiation means, a second light irradiation means, an imaging means, and an orientation determination means. The first light irradiation means and the second light irradiation means are means which irradiate the fiber bundle group (sheet-shaped fiber bundle group) having a sheet shape formed on the belt-shaped resin (resin sheet) running in one direction with light obliquely from the upper side in directions intersecting each other, as viewed in a plan view. The imaging means is provided above the sheet-shaped fiber bundle group and is a means for imaging a still image of the upper surface of the sheet-shaped fiber bundle group in the state where the fiber bundle group is irradiated with the light from the first light irradiation means or the second light irradiation means. The orientation determination means is a means for determining the fiber orientation state of the sheet-shaped fiber bundle group. Specifically, the orientation determination means is configured to calculate the luminance difference or the luminance ratio between the luminance in the state of being irradiated with the light from the first light irradiation means and the luminance in the state of being irradiated with the light from the second light irradiation means on the basis of the luminance information obtained from the still image captured by the imaging means.

Hereinafter, an example of the fiber bundle group inspection device according to the invention will be further described with reference to FIGS. 10 to 13. The fiber bundle group inspection device 2100 (hereinafter, simply referred to as the inspection device 2100) according to the embodiment inspects the fiber orientation state of a sheet-shaped fiber bundle group F2 configured with a plurality of fiber bundles f continuously scattered on the belt-shaped resin P2 (hereinafter, also referred to as a resin sheet P2) running in one direction. The inspection device 2100 is configured to include a first light irradiation means 2102, a second light irradiation means 2104, an imaging means 2106, and an orientation determination means 2108.

In this example, the first light irradiation means 2102 is configured to include a pair of first irradiation units 2102a and a second irradiation unit 2102b. The first irradiation unit 2102a and the second irradiation unit 2102b are provided obliquely above the fiber bundle group F2 on the outside in the width direction of the belt-shaped resin sheet P2 running in one direction so as to face each other. In the first light irradiation means 2102, the fiber bundle group F2 is irradiated with light obliquely downward from the first irradiation unit 2102a and the second irradiation unit 2102b in a direction perpendicular to the longitudinal direction (running direction) of the resin sheet P2 as viewed in a plan view.

The first irradiation unit 2102a and the second irradiation unit 2102b are elongated members that are elongated in the running direction of the resin sheet P2 and have elongated light irradiation surfaces on the side surface of the fiber bundle group F2 side. In the first light irradiation means 2102, the first irradiation unit 2102a and the second irradiation unit 2102b illuminate a certain range interposed between the first irradiation unit 2102a and the second irradiation unit 2102b on the upper surface of the fiber bundle group F2. In the invention, it is preferable that the first light irradiation means is such an elongated member.

Figure 13:
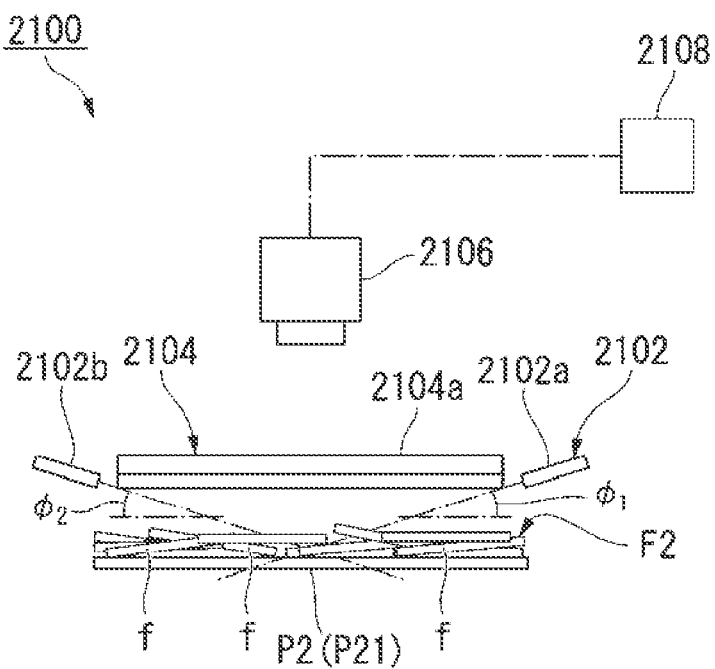
FIG. 13 is a side view of the inspection device of FIG. 10 as viewed from a fourth irradiation unit side of the resin and fiber bundle group.

As illustrated in FIG. 13, the first irradiation unit 2102a is provided to be inclined so that the upper surface of the fiber bundle group F2 is irradiated obliquely downward with the light as viewed in a side view. The inclination angle $\phi_1$ (FIG. 13) of the first irradiation unit 2102a with respect to the horizontal direction is preferably in a range of 10 to 60°, and more preferably in a range of 20 to 45°. If the inclination angle $\phi_1$ is within the above-described range, it is easy to obtain sufficient luminance information, and it is easy to determine the fiber orientation state of the fiber bundles front the luminance difference and the luminance ratio.

Similarly to the first irradiation unit 2102a, the second irradiation unit 2102b is provided to be inclined so that the upper surface of the fiber bundle group F2 is irradiated obliquely downward with the light. The inclination angle $\phi_2$ (FIG. 13) of the second irradiation unit 2102b with respect to the horizontal direction is preferably in a range of 10 to 60°, more preferably in a range of 20 to 45° for the same reason as the inclination angle $\phi_1$ of the first irradiation unit 2102a with respect to the horizontal direction.

It is preferable that the inclination angle $\phi_1$ and the inclination angle $\phi_2$ are the same. In addition, the inclination angle $\phi_1$ and the inclination angle $\phi_2$ may be different.

As a light source in the first light irradiation means, any light source may be employed as long as the luminance information can be obtained by capturing the still image of the upper surface of the sheet-shaped fiber bundle group in the state where the fiber bundle group is irradiated with light by the first light irradiation means. As a specific example of the light source, there may be exemplified a white light emitting diode (white LED), a fluorescent lamp, a halogen lamp, a metal high land lamp, and the like. As the first light irradiation means, there may be exemplified a light irradiation means having an irradiation unit provided with an elongated light irradiation surface and provided with a white LED and a light diffusing plate.

Figure 10:
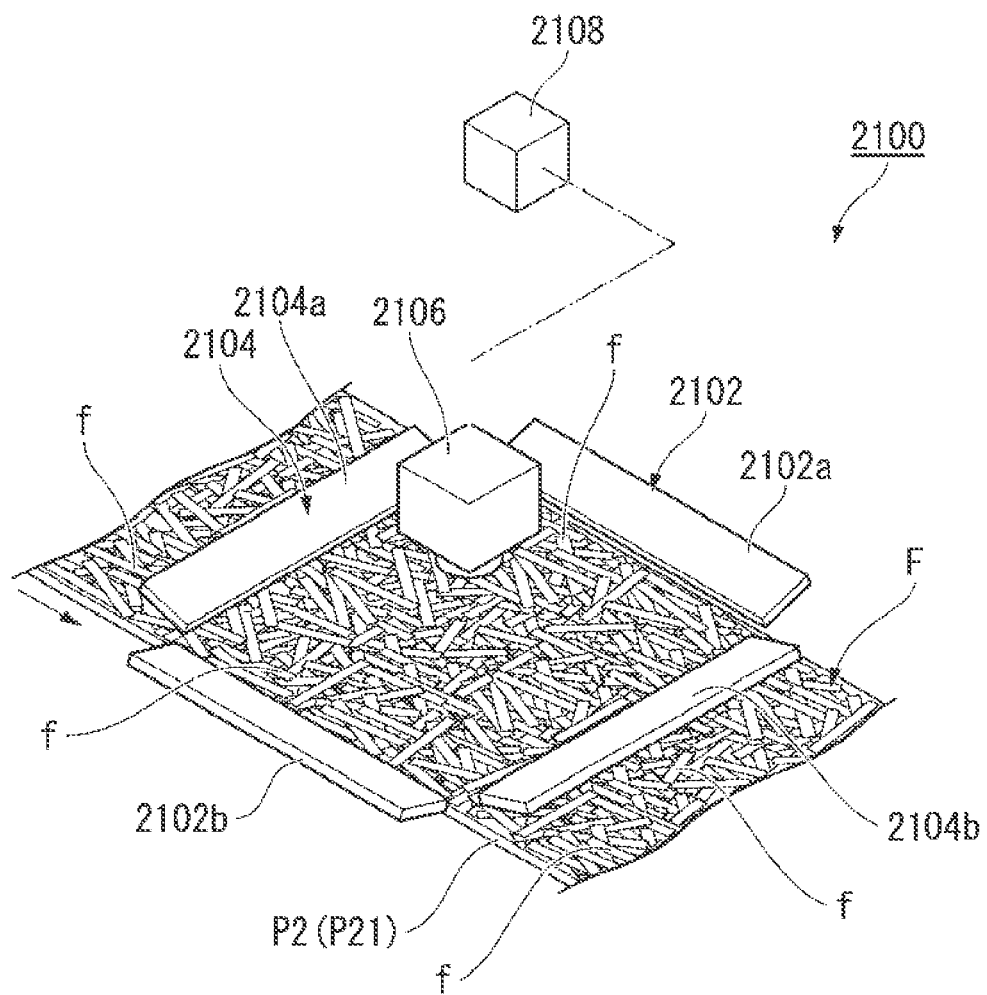
FIG. 10 is a perspective view illustrating an example of an inspection device for a fiber bundle group according to the invention.
Figure 11:
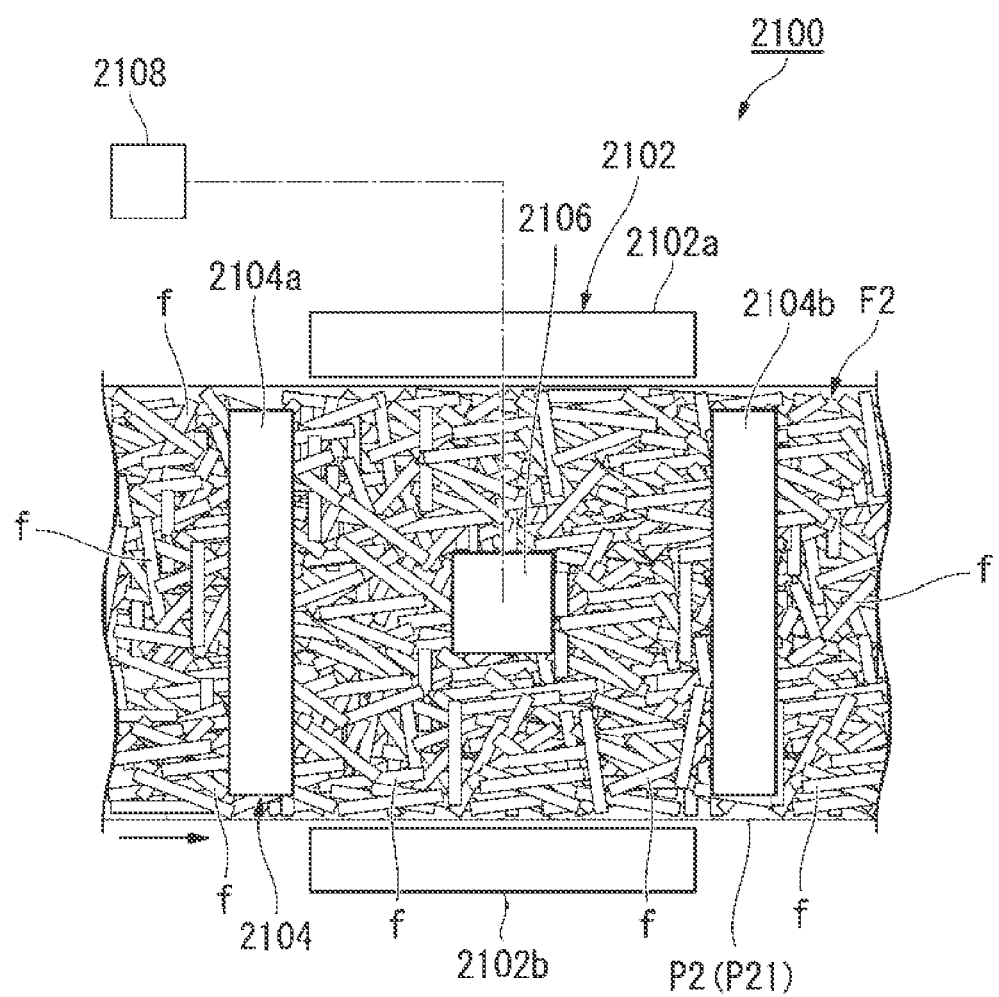
FIG. 11 is a plan view of the inspection device of FIG. 10.
Figure 12:
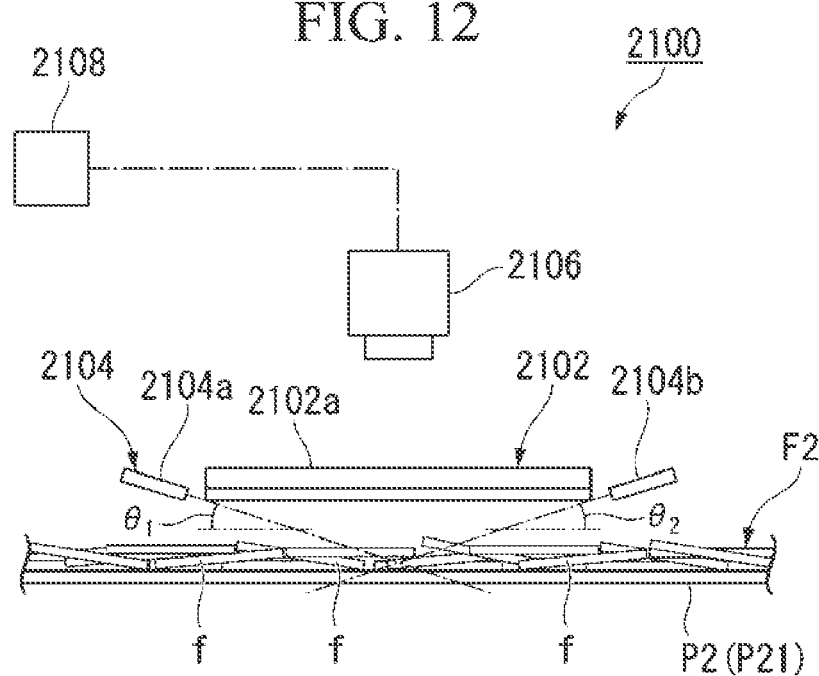
FIG. 12 is a side view of the inspection device of FIG. 10 as viewed from a second irradiation unit side of the resin and fiber bundle group.

In addition, the first light irradiation means is not limited to a light irradiation means having a pair of irradiation units, and the first light irradiation means be configured with only one irradiation unit.

in this example, the second light irradiation means 2104 is configured to include a pair of third irradiation units 2104a and a fourth irradiation unit 2104b. As illustrated in FIGS. 10 to 12, the third irradiation unit 2104a and the fourth irradiation unit 2104b are arranged on both sides of the first irradiation unit 2102a and the second irradiation unit 2102b in the running direction of the resin sheet P2 above the fiber bundle group F2 so as to face each other.

In the second light irradiation means 2104, the fiber bundle group F2 is irradiated with light by the third irradiation unit 2104a and the fourth irradiation unit 2104b obliquely downward and in the longitudinal direction (running direction) of the resin sheet P2 as viewed in a plan view. In the inspection device 2100, the light irradiation direction from the first light irradiation means 2102 and the light irradiation direction from the second light irradiation means 2104 are perpendicular to each other as viewed in a plan view. Thus, in the invention, it is preferable that the light irradiation direction from the first light irradiation means and the light irradiation direction from the second light irradiation means are perpendicular to each other, as viewed in a plan view. Therefore, it is easy to determine the fiber orientation state of the fiber bundle from the luminance difference and the luminance ratio.

In addition, in the invention, the light irradiation direction from the first light irradiation means and the light irradiation direction from the second light irradiation means may not be perpendicular to each other as viewed in a plan view. The angle between the light irradiation direction from the first light irradiation means and the light irradiation direction from the second light irradiation means as viewed in a plan view is preferably in a range of 60 to 120°, more preferably in a range of 80 to 100°. If the angle is within the range, it is easy to determine the fiber orientation state of the fiber bundle from the luminance difference and the luminance ratio.

The third irradiation unit 2104a and the fourth irradiation unit 2104b are elongated members that are elongated in the width direction of the resin sheet P2 and have elongated light irradiation surfaces on the side surface facing the fiber bundle group F2. In the second light irradiation means 2104, the third irradiation unit 2104a and the fourth irradiation unit 2104b illuminate a certain range interposed between the third irradiation unit 2104a and the fourth irradiation unit 2104b on the upper surface of the fiber bundle group F2. In the invention, it is preferable that one having the elongated light source is used as the second light irradiation means. The range of irradiation of the light by the second light irradiation means 2104 on the upper surface of the fiber bundle group F2 is a range equivalent to the range irradiated by the first light irradiation means 2102.

As illustrated in FIG. 12, the third irradiation unit 2104a is provided to be inclined so that the upper surface of the fiber bundle group F2 is irradiated obliquely downward with the light. The inclination angle $\theta_1$ (FIG. 12) of the third irradiation unit 2104a with respect to the horizontal direction is preferably in a range of 10 to 60°, and more preferably in a range of 20 to 45'. If the inclination angle $\theta_1$ is within the above-described range, it is easy to obtain sufficient luminance information, and it is easy to determine the fiber orientation state of the fiber bundles from the luminance difference and the luminance ratio.

Similarly to the third irradiation unit 2104a, the fourth irradiation unit 2104b is provided to be inclined so that the upper surface of the fiber bundle group F2 is irradiated obliquely downward with the light. The inclination angle $\theta_2$ (FIG. 12) of the fourth irradiation unit 2104b with respect to the horizontal direction is preferably in a range of 10 to 60°, more preferably in a range of 20 to 45° for the same reason as the inclination angle $\theta_1$ of the third irradiation unit 2104a with respect to the horizontal direction.

It is preferable that the inclination angles $\phi_1$, $\phi_2$, $\theta_1$, and $\theta_2$ are the same from the viewpoint of easy determination of the fiber orientation state of the fiber bundle from the luminance difference and the luminance ratio. Though all the inclination angles are not necessarily the same, since the luminance varies depending on the inclination angle, it is necessary that $\phi_1=\theta_1$, $\phi_2=\theta_2$, or $\phi_1=\theta_2$, and $\phi_2=\theta_1$.

As the light source in the second light irradiation means, any light source may be used as long as the luminance information can be obtained by capturing the still image of the upper surface of the fiber bundle group in the state where the light irradiated from the second light irradiation means is reflected, and the same light source as the light source in the first light irradiation means can be used. It is preferable that the light source of the first light irradiation means and the light source of the second light irradiation means are the same from the viewpoint of easy determination of the fiber orientation state of the fiber bundle from the luminance difference and the luminance ratio in the orientation determination means. As the second light irradiation means, there may be exemplified a light irradiation means having an irradiation unit provided with an elongated light irradiation surface and provided with a white LED and a light diffusion plate.

In addition, the second light irradiation means is not limited to a light irradiation means having a pair of irradiation units, and the second light irradiation means may be configured with only one irradiation unit.

The imaging means 2106 is arranged above the center of the portion surrounded by the first irradiation unit 2102a, the second irradiation unit 2102b, the third irradiation unit 2104a and the fourth irradiation unit 2104b so as to rapture an image or the upper surface of the fiber bundle group F2. The imaging means 2106 can capture the still image of a portion irradiated with light by the first light irradiation means 2102 or the second light irradiation means 2104 on the upper surface of the fiber bundle group F2.

As the imaging means, any imaging means may be employed as long as the imaging means can capture a still image from which the luminance information in the state of being irradiated with light by the first light irradiation means or the second light irradiation means can be obtained. As the imaging means, there may be exemplified an imaging means having a monochrome optical sensor corresponding to the light source of the first light irradiation means or the second light irradiation means.

The orientation determination means 2108 is electrically connected to the imaging means 2106 and is configured to obtain the luminance information from a still image captured by the imaging means 2106. The orientation determination means 2108 measures the luminance due to the reflected light of the upper surface of the fiber bundle group F2 in the state of being irradiated with light by the first light irradiation means 2102 and the luminance due to the reflected light of the upper surface of the fiber bundle group F2 in the state of being irradiated with light by the second light irradiation means 2104 and calculates the luminance difference or the luminance ratio thereof.

The orientation determination means is not particularly limited as long as the orientation determination means has a processing function of calculating the luminance difference or the luminance ratio from the captured still image. As the orientation determination means, there may be exemplified an orientation determination means configured to include a processing unit for processing a still image to obtain luminance information and calculating a luminance difference or a luminance ratio, a storage unit for storing a threshold value of an externally input luminance difference or luminance ratio, and a determination unit for comparing the luminance difference or the luminance ratio obtained by the processing unit with the threshold value stored in the storage unit to determine the fiber orientation state. In addition, in the case where a control means for controlling the manufacturing conditions is provided on the production line of the fiber-reinforced resin material in accordance with the determination result of the orientation determination means, it is preferable that the orientation determination means is configured to include an interface unit for transmitting the determination result of the determination unit to the control means.

Figure 14A:
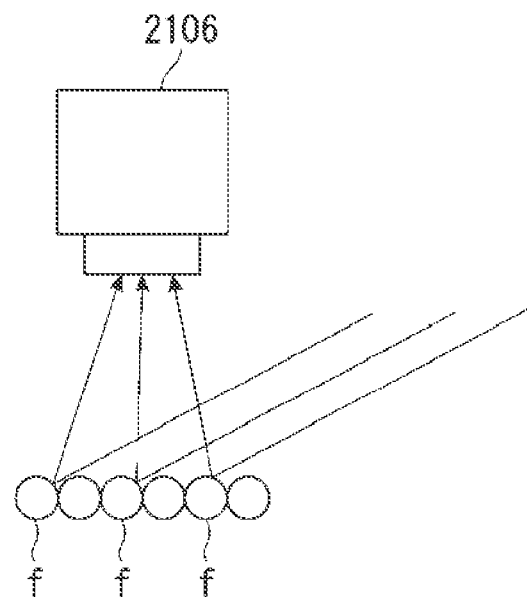
FIG. 14A is a schematic view illustrating a state where light is reflected on a surface of a fiber bundle and is a view illustrating a case where a fiber axis direction and a light running direction are perpendicular to each other as viewed in a plan view.
Figure 14B:
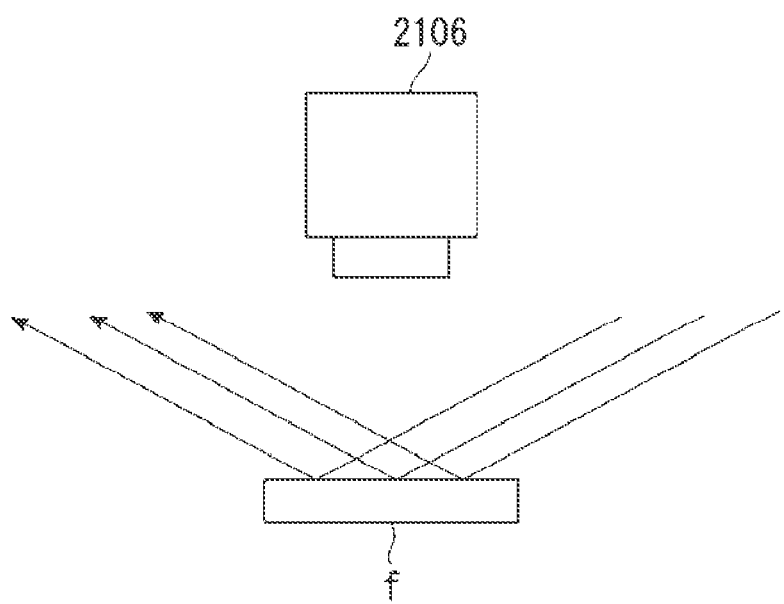
FIG. 14B is a schematic view illustrating a state where light is reflected on a surface of a fiber bundle and is a view illustrating a case where a fiber axis direction and a light running direction are parallel to each other as viewed in a plan view.

In the inspection device 2100, the fiber bundle group F2 formed on the strip-shaped resin sheet P2 running in one direction can be irradiated with light by each of the first light irradiation means 2102 and the second light irradiation means 2104 obliquely from the upper side. Then, the imaging means 2106 can capture a still image of the upper surface of the fiber bundle group F2 in the state of being irradiated with light by the first light irradiation means 2102 or the second light irradiation means 2104. At this time, as illustrated in FIG. 14A, as the angle formed by the running direction of the light as viewed in a plan view and the fiber axis direction of the fiber bundle f is closer to perpendicular, the reflection angle of the light reflected on the surface of the fiber bundle f is larger, and thus, it becomes easy for the reflected light to reach the upper imaging means 2106. On the other hand, as illustrated in FIG. 14B, as the angle formed by the running direction of the light as viewed in a plan view and the fiber axis direction of the fiber bundle f is closer to parallel, the reflection angle of the light reflected on the surface of the fiber bundle f is smaller, and thus, it becomes difficult for the reflected light to reach the upper imaging means 2106.

In the state where the fiber bundle group F2 is irradiated with light by the first light irradiation means 2102, the light propagates in the width direction of the resin sheet P2 as viewed in a plan view. In the still image captured by the imaging means 2106 in this state, as the fiber axis direction of the fiber bundle f becomes closer to the longitudinal direction of the resin sheet P2, the luminance is increased. For this reason, in the state of being irradiated with light by the first light irradiation means 2102, as the number of the fiber bundles f of which fiber axis direction is close to the longitudinal direction of the resin sheet P2 becomes larger, the area of the bright portion due to the reflected light in the fiber bundle group F2 in the still image is increased, and the luminance is increased. On the other hand, in the state where the fiber bundle group F2 is irradiated with light by the second light irradiation means 2104, the light propagates in the longitudinal direction of the resin sheet P2 as viewed in a plan view. In the still image captured by the imaging means 2106 in this state, as the fiber axis direction of the fiber bundle f becomes closer to the width direction or the resin sheet P2, the luminance is increased. For this reason, in the state of being irradiated with light by the second light irradiation means 2104, as the number of the fiber bundles f of which fiber axis direction is close to the width direction of the resin sheet P2 becomes larger, the area of the bright portion due to the reflected light in the fiber bundle group F2 in the still image is increased, and the luminance is increased.

In this manner, from the comparison of the luminances of the same ranges obtained from the still images of the fiber bundle group F2 in the state of being irradiated with light by the first light irradiation means 2102 and in the state of being irradiated with light by the second light irradiation means 2104, the proportion of the fiber bundles f of which fiber axis direction is close to the longitudinal direction of the resin sheet P2 and the proportion of the fiber bundles f of which fiber axis direction is close to the width direction of the resin sheet P2 can be known. Therefore, the fiber orientation state of the fiber bundle group F2 can be determined. Specifically, the orientation determination means 2108 calculates the luminance difference or luminance ratio between the luminances of the states. The smaller the absolute value of the luminance difference is, the more random the fiber orientation is; and the larger the absolute value of the luminance difference, the more deviated the fiber orientation of the fiber bundle f is. In addition, the closer to 1 the luminance ratio is the more random the fiber orientation and the farther away from 1 the luminance ratio is, the more deviated the fiber orientation of the fiber bundle f is.

As described above, by using the fiber bundle group inspection device according to the invention, it is possible to easily inspect the fiber orientation state of the fiber bundle in the running fiber bundle group even on the production line of the fiber-reinforced resin material.

In addition, the fiber bundle group inspection device according to the invention is not limited to the inspection device 2100 described above. For example, each of the first light irradiation means and the second light irradiation means may be an inspection device configured with one irradiation unit. In addition, the inspection device may be arranged such that the first light irradiation means is deviated to the upstream side or the downstream side of the second fight irradiation means in the running direction of the resin sheet. In this case, two imaging means corresponding to the first light irradiation means and the second light irradiation means are provided.

In addition, the light irradiation directions as viewed in a plan view from the first light irradiation means and the second light irradiation means may be deviated from the width direction and the longitudinal direction of the resin sheet. However, it is preferable that light irradiation directions as viewed in a plan view from the first light irradiation means and the second light irradiation means coincide with the width direction and the longitudinal direction of the resin sheet, respectively.

The fiber bundle group inspection device according to the invention can be appropriately used for the device for manufacturing a fiber-reinforced resin material according to the invention. Ira addition, the fiber bundle group inspection device according to the invention a to be installed in a device for manufacturing a fiber-reinforced resin material without a scattering unit and used for inspection of the fiber bundle group on the production line.

(Fiber Bundle Group Inspecting Method)

Hereinafter, a fiber bundle group inspecting method will be described. The fiber bundle group inspecting method includes the following imaging step and orientation determining step.

Imaging Step: A sheet-shaped fiber bundle group configured with a plurality of fiber bundles continuously scattered on a belt-shaped resin (resin sheet) running in one direction is irradiated separately with the first light and the second light obliquely from the upper side, and a still image of the upper surface of the fiber bundle group in the state of being irradiated with the first light or the second light is captured.

Orientation Determining Step: On the basis of luminance information obtained from the still image captured in the imaging step, the luminance difference or the luminance ratio between the luminance in the state of being irradiated with the first light and the luminance in the state of being irradiated with the second light is calculated to determine the fiber orientation state of the fiber bundle group.

Hereinafter, a method of inspecting the sheet-shaped fiber bundle group will be described by taking the case of using the inspection device 2100 as an example.

<Imaging Step>

The fiber bundle group F2 configured with a plurality of fiber bundles f continuously scattered on the belt-shaped resin sheet P2 running in one direction is irradiated with the first light obliquely from the upper side by the first light irradiation means 2102. Then, in the state of being irradiated with the first light by the first light irradiation means 2102, the imaging means 2106 captures the still image of the upper surface of the fiber bundle group F2. In addition, the irradiation of the first light by the first light irradiation means 2102 is stopped, and the fiber bundle group F2 is irradiated with the second light by the second light irradiation means 2104 obliquely from the upper side. Then, in the state of being irradiated with the second light by the second light irradiation means 2104, the imaging means 2106 captures the still image of the upper surface of the fiber bundle group F2. In this example, the first light irradiated from the first light irradiation means 2102 and the second light irradiated from the second light irradiation means 2104 are perpendicular to each other as viewed in a plan view.

The capturing of the still images in the state of being irradiated with the first light by the first light irradiation means 2102 and in the state of being irradiated with the second light by the second light irradiation means 2104 is performed so that at least a portion of the respective imaging ranges is overlaid in order to compare the luminance in the same range. Specifically, for example, the capturing of the still image is performed by switching the state of being irradiated with light by the first light irradiation means 2102 and the state of being irradiated with light by the second light irradiation means 2104 every 100 ms.

<Orientation Determining Step>

The orientation determination means 2108 measures the luminance in a specific range of the upper surface of the fiber bundle group F2 from the still image in the state of being irradiated with the first light by the first light irradiation means 2102. In addition, the orientation determination means measures the luminance in the same range as the specific range of the upper surface of the fiber bundle group F2 from the still image in the state of being irradiated with the second light by the second light irradiation means 2104. In addition, the orientation determination means calculates the luminance difference or the luminance ratio between the luminance in the state of being irradiated with the first light and the luminance in the state of being irradiated with the second light from these luminances and determines the fiber orientation state of the fiber bundle group F2. For example, in the case of desiring to manufacture a fiber-reinforced resin material excellent in the isotropy of mechanical properties, as the favorable absolute value of the luminance difference becomes smaller, it can be determined that the fiber orientation is good, that is, random. In addition, as the luminance ratio is closer to 1, it can be determined that the fiber orientation is good, that is, random.

According to the fiber bundle group inspecting method described above, it is possible to easily inspect the fiber orientation state of the fiber bundle in the running fiber bundle group even on the production line of the fiber reinforced resin material. The Fiber bundle group inspecting method is not limited to the above-described method using the inspection device 2100, and another inspection device exemplified in the description of the inspection device may be employed. For example, in the case where the first light irradiation means is arranged to be shifted to the upstream side or the downstream side of the second light irradiation means, the imaging means corresponding to each of the first light irradiation means and the second light irradiation means may perform sequential imaging so that the imaging ranges overlay each other.

The fiber bundle group inspecting method described above can be appropriately used for a method for manufacturing a fiber-reinforced resin material described later. In addition, the fiber bundle group inspecting method described arose may be used for inspecting a fiber bundle group on a production line in a method for manufacturing a fiber-reinforced resin material using a manufacturing device not including a scattering unit. For example, a method for manufacturing a fiber-reinforced resin material having an isotropy by changing the conveying speed of the first sheet or the like on the basis of the determination result according to the inspecting method and adjusting the fiber direction of each fiber bundle so as to be aligned with the conveying direction of the first sheet may be employed.

(Device for Manufacturing, Fiber-Reinforced Resin Material)

Figure 15:
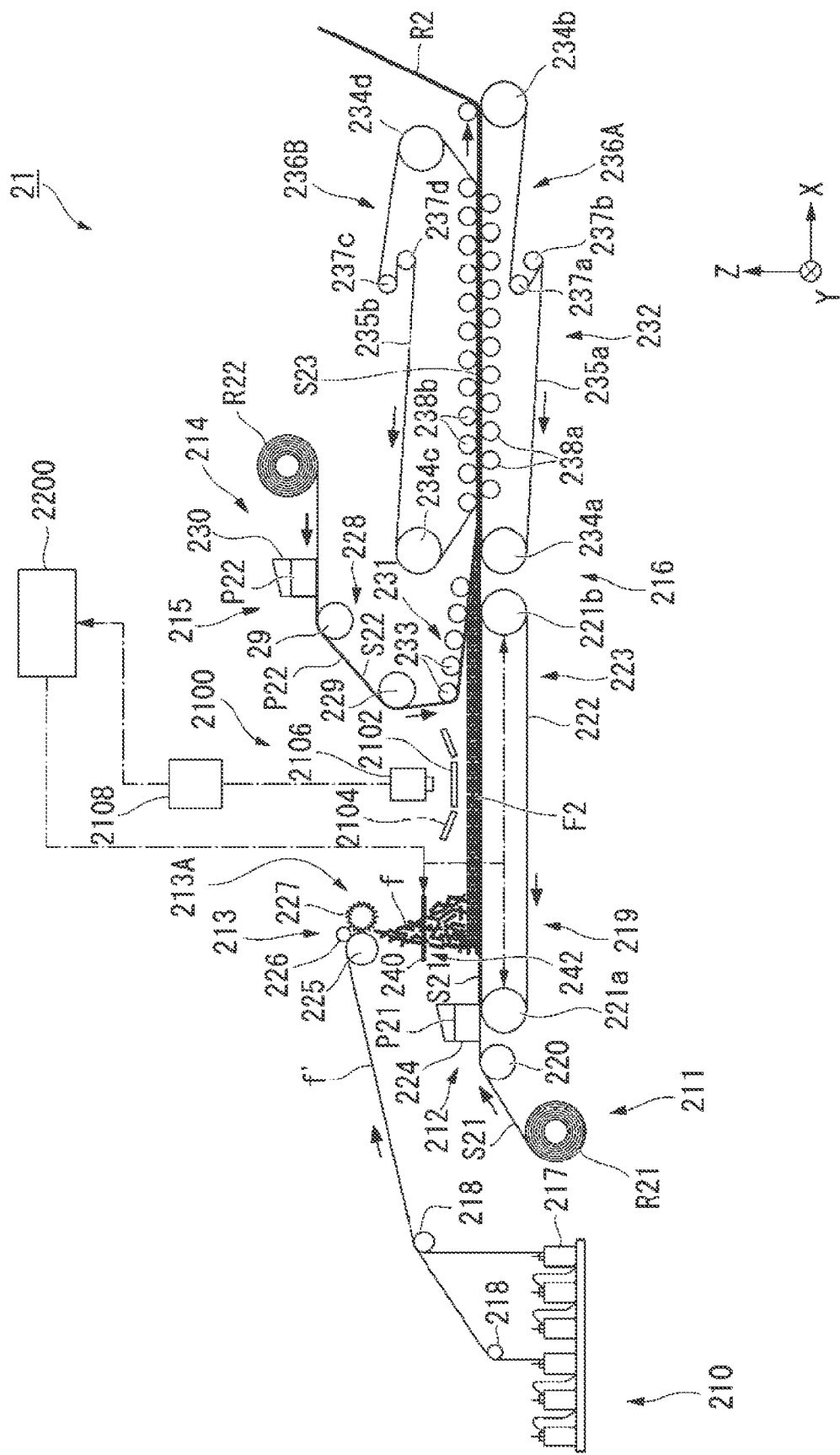
FIG. 15 is a side view illustrating an example of a device for manufacturing a fiber-reinforced resin material according to one embodiment of the invention.

Hereinafter, as an example of a device for manufacturing a fiber-reinforced resin material according to Example 2, which is an example of inspecting the fiber orientation state of the fiber bundle group on the production line, a manufacturing device for manufacturing, an SMC where a paste containing a thermosetting resin is impregnated between the fiber bundles will be described. The device 21 for manufacturing a fiber-reinforced resin material (hereinafter, simply referred to as the manufacturing device 21) according to the embodiment will be described with reference to FIG. 15. FIG. 15 is a schematic configuration view illustrating a configuration of the manufacturing device 21. In addition, in the following description, similarly to the manufacturing device 11, an XYZ rectangular coordinate system is set, and a positional relationship of each member will be described with reference to the XYZ rectangular coordinate system as necessary.

The manufacturing device 21 is configured to include a fiber bundle supply unit 210, a first sheet supply unit 211, a first conveying unit 219, a first coating unit 212, a cutting unit 213, a scattering unit 242, a second sheet supply unit 214, a second conveying unit 228, a second coating unit 215, an impregnation unit 216, an inspection device 2100, and a control means 2200.

The first sheet supply unit 211 supplies the elongated first sheet (carrier sheet) S21 unwound from the first raw fabric roll R21 to the first conveying unit 219. The first conveying unit 219 is provided with a guide roll 220 and a conveyor 223 on which the endless belt 222 is hung between the pair of pulleys 221a and 221b. The guide roll 220 guides the first carrier sheet S21 supplied from the first sheet supply unit 211 toward the conveyor 223 while rotating. The conveyor 223 revolves the endless belt 222 by rotating the pair of pulleys 221a and 221b in the same direction and conveys the first sheet S21 to the right side (+X axis direction) in the X axis direction on the surface of the endless belt 222.

The first coating unit 212 is located immediately above the pulley 221a on the side of the guide roll 220 in the first conveying unit 219 and is provided with a supply box 224 for supplying the paste P21 containing a thermosetting resin. A slit (not shown) is formed on the bottom surface of the supply box 224, so that the paste P21 with a predetermined thickness from the slit is applied on the surface of the conveyed first sheet S21. The coated paste P21 runs with the conveyance of the first sheet S21.

The fiber bundle supply unit 210 draws out the elongated fiber bundle f' from the plurality of bobbins 217 and supplies the elongated fiber bundle to the cutting unit 213 through the plurality of guide rolls 218. The cutting unit 213 is located above the first sheet S21 at the downstream side in the conveying direction with respect to the first coating unit 112. The cutting unit 213 is configured to include a cutting machine 213A that continuously cuts the fiber bundles f' supplied from the fiber bundle supply unit 210 into a predetermined length. The cutting machine 213A is configured to include a guide roller 225, a pinch roller and a cutter roller 227. The guide roller 225 guides the fiber bundles f' supplied from the fiber bundle supply unit 210 downward while rotating. The pinch roller 226 rotates in the direction opposite to the guide roller 225 while interposing the fiber bundles f' with the guide roller 25. Therefore, the fiber bundles f' are drawn out from the plurality of bobbins 217. The cutter roller 227 cuts the fiber bundle f' while rotating so as to have a predetermined length. The fiber bundles f cut to have a predetermined length by the cutting machine 213A are dropped and scattered on the paste P21 to form a sheet-shaped fiber bundle group F2.

The scattering unit 242 is arranged between the paste P21 applied on the first sheet S21 and the cutting machine 213A. The scattering unit 242 includes the plurality of rods 140. As in the first embodiment, the plurality of rods 240 are arranged in parallel to each other with a space therebetween in the width direction (Y axis direction) of the first sheet S21 as viewed in a plan view so that the longitudinal direction thereof becomes the longitudinal direction (X axis direction) of the first sheet S21. Each of the rods 240 is supported, for example, in a manner that one end of each rod 240 is attached to the support rod. The fiber bundles f that are in contact with the rods 240 among the fiber bundles f that are cut by the cutting machine 213A and dropped tend to collapse in directions different from the running direction of the first seat S21. Therefore, it is possible to uniformly disperse the fiber bundles f on the paste P21 applied on the first sheet S21 without directionality while suppressing generation of fluff (fiber scraps) from the fiber bundle f.

As an appearance of each of the rods 240, the same appearance as each of the rods 140 of the first embodiment may be exemplified, and preferred appearances are also the same. Specifically, the height of each of the rods 240 from the first sheet S21 can be appropriately set. The cross-sectional shape of the rod 240 may be a circle, a rectangle, a polygon, or the like, and a circular shape is preferable. The diameter of each of the rods 240 may be set to be, for example, in a range of about 0.1 to 10 mm.

The interval between the adjacent rods 240 as viewed in a plan view is preferably in a range of 0.9 to 1.6 times the average length of the fiber bundles f cut by the cutting machine 213A. If the interval is equal to or larger than the lower limit value, the fiber bundle f is less likely to be deposited between the rods 240. If the interval is equal to or smaller than the upper limit value, since a sufficient proportion of the fiber bundles f are in contact with the rods 240, the fiber bundle group F2 having random fiber orientation tends to be formed.

Figure 16:
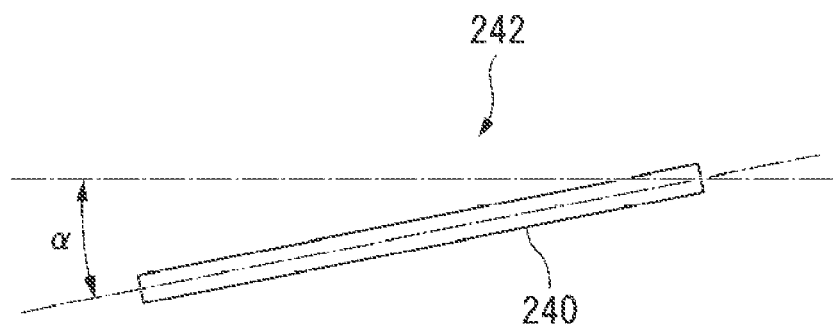
FIG. 16 is a side view illustrating the inclination angle of the rod in the manufacturing device of FIG. 15.

It is preferable that the rods 240 are close to the horizontal direction from the viewpoint of easy formation of the fiber bundle group F2 in which the fiber bundles f are scattered in random fiber orientations. In the case where the rods 240 are allowed to be inclined, the inclination angle α (FIG. 16) of the rods 240 with respect to the horizontal direction is preferably larger than 0° and equal to or smaller than 40°.

The rods 240 may be allowed to be vibrated. In this case, the direction in which the rods 240 is allowed to vibrate may be any one of the longitudinal direction (X axis direction), the width direction (Y axis direction), and the height direction (Z axis direction). The rods 240 may be vibrated in a plurality of directions.

The second sheet supply unit 214 supplies the elongated second sheet (carrier sheet) S22 unwound from the second raw fabric roll R22 to the second conveying unit 228. The second conveying unit 228 is located above the first sheet S21 conveyed by the conveyor 223 and is provided with a plurality of guide rolls 229. The second conveying unit 228 conveys the second sheet S22 supplied front the second sheet supply unit 214 in a direction (left side in the X axis direction) opposite to the first sheet S21 and, after that, reverses the conveying direction to the same direction as the first sheet S21 by the plurality of guide rolls 229.

The second coating unit 215 is located immediately above the second sheet S22 being conveyed in a direction opposite to that of the first sheet S21 and is provided with a supply box 230 for supplying the paste P21 containing a thermo-setting resin. A silt (not shown) is formed on the bottom surface of the supply box 230, so that the paste P21 with a predetermined thickness from the slit is applied on the surface of the conveyed second sheet S22. The coated paste P21 runs with the conveyance of the second sheet S22.

The impregnation unit 216 is located on the downstream side of the cutting machine 213A in the conveying direction and is provided with a bonding mechanism 231 and a pressing, mechanism 232. The bonding mechanism 231 is located above the other pulley 221b of the conveyor 223 and is provided with a plurality of bonding rolls 233. The plurality of bonding rolls 233 are arranged side by side in the conveying direction in the state of being in contact with the hack surface of the second sheet S22 on which the paste P21 is formed. In addition, the plurality of bonding rolls 233 are arranged so that the second sheet S22 gradually approaches the first sheet S21.

In the bonding mechanism 231 the first sheet S21 and the second sheet S22 are conveyed while being overlaid in the state of interposing the paste P21, the fiber bundle group F2 and the paste P21 therebetween. Herein, the one in which the first sheet S21 and the second sheet S22 are bonded while interposing the paste P21, the fiber bundle group F2, and the paste P21 is referred to as a bonding sheet S23.

The pressing mechanism 232 is located on the downstream side of the bonding mechanism 231 and is provided with a lower conveyor 236A having an endless belt 235a hung between a pair of pulleys 234a and 234b and an upper conveyor 236B having an endless belt 235b hung between a pair of pulleys 234c and 234d. The lower conveyor 236A and the upper conveyor 236B are arranged to face each other in the state where the endless belts 235a and 235b abut each other.

In the pressing mechanism 232, by rotating the pair of pulleys 234a and 234b of the lower conveyor 236A in the same direction, the endless belt 235a is revolved. In addition, in the pressing mechanism 232, by rotating the pair of pulleys 234c, 234d of the upper conveyor 236B in the same direction, the endless belt 235b is revolved in the opposite direction at the same speed as the endless belt 235a. Therefore, the bonding sheet S23 interposed between the endless belts 235a and 235b is conveyed to the right side in the X axis direction.

A pair of tension pulleys 237a and 237b for adjusting the tension applied to the endless belt 235a is arranged in the lower conveyor 236A. Similarly, a pair of tension pulleys 237c and 237d for adjusting the tension applied to the endless belt 235a are arranged in the upper conveyor 236B. These tension pulleys 237a, 237b, 237c, and 237d are provided on the side opposite to the abutting portion of the endless belts 235a, 235b.

The pressing mechanism 232 is further provided with a plurality of lower rolls 238a and a plurality of upper rolls 238b. The plurality of lower rolls 238a are arranged side by side in the conveying direction in the state of being in contact with the back surface of the abutting portion of the endless belt 235a. Similarly, the plurality of upper rolls 238b are arranged side by side in the conveying direction in the state of being in contact with the back surface of the abutting portion of the endless belt 235b. In addition, the plurality of loser rolls 238a and the plurality of upper rolls 238b are alternately arranged side by side in the conveying direction of the bonding sheet S23.

In the pressing mechanism 232, while the bonding sheet S23 passes between the endless belts 235a and 235b, the paste P21, the fiber bundle group F2, and the paste P21 interposed between the first sheet S21 and the second sheet S22 are pressed by the plurality of lower rolls 238a and the plurality of upper rolls 238b. At this time, the paste P21 is impregnated into the fiber bundle group F2. Therefore, the raw fabric R2 of the fiber-reinforced resin material (SMC) is obtained. The raw fabric R2 can be cut into a predetermined length to be used for molding. In addition, the first sheet S21 and the second sheet S22 are peeled off from the SMC before molding the SMC.

The inspection device 2100 is provided above the first sheet S21 between the cutting machine 213A and the bonding mechanism 231. Specifically, as illustrated in FIGS. 10 to 13, the first irradiation unit 2102a and the second irradiation unit 2102b of the first light irradiation means 2102 are arranged obliquely above the fiber bundle group F2 on the outer side in the width direction of the paste P21 so as to face each other. In addition, the third irradiation unit 2104a and the fourth irradiation unit 2104b of the second light irradiation means 2104 are arranged above the fiber bundle group F2 on both sides of the first irradiation unit 2102a and the second irradiation unit 2102b in the running direction of the paste P21 so as to face each other. In addition, the imaging means 2106 is provided above the center of the portion surrounded by the first irradiation unit 2102a, the second irradiation unit 2102b, the third irradiation unit 2104a, and the fourth irradiation unit 2104b. In addition, the orientation determination means 2108 electrically connected to the imaging means 2106 is provided.

The control means 2200 is electrically connected to the orientation determination means 2108, and the result of the determination by the orientation determination means 2108 is transmitted. The control means 2200 is configured to control the inclination angle α and the vibration frequency of the rods 240 with respect to the horizontal direction. In addition, the control means 2200 adjusts the rotation of the pair of pulleys 221a and 221b in the first conveying unit 219 and controls the speed of the conveyor 223, so that the running speed of the paste P21 running together with the conveyed first sheet S21 can be controlled.

In addition, the device for manufacturing a fiber-reinforced resin material provided with the inspection device is not limited to the manufacturing device 21 described above. For example, instead of the scattering unit 242 having the plurality of rods 240, a scattering unit having a gas diffuser or blowing a gas such as air to the fiber bundles f that are cut and dropped may be installed. In addition, the device for manufacturing a fiber-reinforced resin material provided with the inspection device may be a manufacturing device for manufacturing a fiber-reinforced resin material used for a stampable sheet using a thermoplastic resin instead of a thermosetting resin.

(Method for Manufacturing Fiber-Reinforced Resin Material)

In the method tier manufacturing a fiber-reinforced resin material according to the invention, an inspecting step of inspecting the fiber orientation state of fiber bundles scattered on the resin after the scattering step can be included. In the method for manufacturing a fiber-reinforced resin material including an inspecting step, it is preferable that the inspecting step includes the following imaging step and orientation determining step.

Imaging Step: The fiber bundle group formed by dispersing the cut fiber bundles in the resin is irradiated with the first light and the second light separately obliquely from the upper side in directions intersecting each other as viewed in a plan view, and the still image of the upper surface of the fiber bundle group in the state of being irradiated with the first light or the second light is captured.

Orientation Determining Step: On the basis of luminance information obtained from the still image captured in the imaging step, the luminance difference or the luminance ratio between the luminance in the state of being irradiated with the first light and the luminance in the state of being irradiated with the second light is calculated to determine the fiber orientation state of the fiber bundle group.

Hereinafter, a method using the manufacturing device 21 will be described as an example of a method for manufacturing a fiber-reinforced resin material according to the second embodiment that includes an inspecting step. The method for manufacturing a fiber-reinforced resin material according to the embodiment is a method for manufacturing a fiber-reinforced resin material (SMC) containing a plurality of fiber bundles and a resin by using the fiber bundle group inspecting method according to the invention described above. The method for manufacturing a fiber-reinforced resin material according to the embodiment is a method including, the following coating step, cutting step, scattering step, inspecting step, impregnating step, and control step.

Coating Step: The paste P21 is allowed to be applied on the first sheet S21 conveyed by the first conveying unit 219.

Cutting Step: An elongated fiber bundle f is allowed to be cut with a cutting machine 213A.

Scattering Step: The cut fiber bundles fare allowed to be dispersed and continuously scattered on the belt-shaped paste P21 which is applied on the first sheet S21 and is running in one direction, by the scattering unit 242 to form a fiber bundle group F2.

Inspecting Step: A fiber orientation state of the fiber bundle group F2 formed on the paste P21 is inspected by the inspection device 2100.

Impregnating Step: After the inspecting step, the paste P21 and the fiber bundle group F2 on the first sheet S21 are allowed to be pressed to impregnate the paste P21 between the fiber bundles f to obtain a fiber-reinforced resin material.

Control Step: A condition of the scattering step is allowed to be changed on the basis of an inspection result of the inspecting step to control the fiber orientation state of the fiber bundle group F2.

<Coating Step>

The first sheet supply unit 211 unwinds the elongated first sheet S21 from the first raw fabric roll R21 and supplies the unwound first sheet S21 to the first conveying unit 219, and the first coating unit 212 applies the paste P21 having a predetermined thickness. The first sheet S21 is conveyed by the first conveying unit 219, so that the paste P21 applied on the first sheet S21 is allowed to run. The thickness of the paste P21 applied on the surface of the first sheet S2.1 is not particularly limited.

The thermosetting resin contained in the paste P21 is not particularly limited, and an unsaturated polyester resin and the like may be exemplified. A filler such as calcium carbonate, a low shrinkage reducing agent, a release agent, a curing initiator, a thickener, or the like may be mixed in the paste P21.

<Cutting Step>

The elongated fiber bundle f is drawn Out from the plurality of bobbins 217 by the fiber bundle supply unit 210 and supplied to the cutting unit 211 and the fiber bundle f is continuously cut with a predetermined length in the cutting machine 213A.

<Scattering Step>

Since the plurality of rods 240 are arranged side by side between the first sheet S21 and the cutting machine 213A, the fiber bundles f cut by the cutting machine 213A are dropped toward the plurality of rods 240. A portion of the fiber bundles f that are cut by the cutting machine 213A and dropped is in contact with the rods 240 and faces in a direction different from the running direction of the first seat S21. Therefore, the fiber bundles f are dispersed, and a sheet-shaped fiber bundle group F2 is formed where the fiber bundles f are scattered in random fiber orientations on the applied paste P21. The thickness of the fiber bundle group F2 is not particularly limited.

The fiber bundle is preferably a carbon fiber bundle. In addition, as the fiber bundle, a glass fiber bundle may be used.

<Inspecting Step>

In the imaging step, the fiber bundle group P2 is irradiated with the first light by the first light irradiation means 2102, and a still image of the upper surface of the fiber bundle group F2 is captured by the imaging means 2106. In addition, the second light irradiation means 2104 irradiates the fiber bundle group F2 with the second light, and the imaging means 2106 captures the still image of the upper surface of the fiber bundle group F2. Next, in the orientation determining step, the orientation determination means 2108 measures the luminance in the state of being irradiated with the first light and the luminance in the state of being irradiated with the second light from each still image, calculates the luminance ratio, and determines the fiber orientation state of the fiber bundle group F2.

<Impregnating Step>

The second sheet supply unit 214 unwinds the elongated second sheet S22 from the second raw fabric roll R22 and supplies the unwound second sheet S22 to the second conveying unit 228. The paste P21 having a predetermined thickness is applied on the surface of the second sheet S22 by the second coating unit 215. The thickness of the paste P21 applied on the second sheet S22 is not particularly limited.

The paste P21 is allowed to run by conveying the second sheet S22, and in the impregnation unit 216, the paste P21 is bonded on the fiber bundle group F2 after the inspection by the bonding mechanism 231. Then, the paste P21, the fiber bundle group F2, and the paste P21 are pressed by the pressing mechanism 232, and the paste P21 is impregnated into the fiber bundle group F2. Therefore, the raw fabric R2 in which the fiber-reinforced resin material is interposed between the first sheet S21 and the second sheet S22 is obtained.

<Control Step>

In the control step, the determination result is transmitted from the orientation determination means 2108 to the control means 2200, and the condition of the scattering step is controlled on the basis of the determination result to adjust the orientation state of each fiber bundle in the fiber bundle group F2.

The running speed of the paste P21 on the first sheet S21 greatly influences the fiber orientation state of the fiber bundle group F2. Since the first sheet S21 is conveyed even after the distal ends of the cut fiber bundles f' land on the paste P21, the fiber direction of each fiber bundle f' is easy to align with the running direction of the first sheet S21. The faster the conveying speed of the first sheet S21 is, the more easily the fiber bundle f' is pulled in the conveying direction of the first sheet S21 before the fiber bundle f' collapse in the direction perpendicular to the conveying direction of the first sheet S21 after landing, and the orientation of the first sheet S21 in the conveying direction becomes conspicuous. For this reason, it is preferable that, in the control step, by adjusting the speed of the conveyor 223 on the basis of the inspection result of the inspecting step, the conveying speed of the first sheet S21 and the running speed of the paste P21 applied on the first sheet S21 are changed, and the orientation state of each fiber bundle in the fiber bundle group F2 is controlled.

For example, in the case where the orientation determination means 2108 determines that the fiber orientation of the fiber bundle group F2 is biased and detective, the control means 2200 controls the conveying speed of the first sheet S21 and the running speed of the paste P21 applied on the first sheet S21 to be lowered, so that the fiber direction of each fiber bundle f is prevented from being aligned with the conveying direction of the first sheet S21. In this manner, in the case where the conveying speed of the first sheet S21 and the running speed of the paste P21 applied on the first sheet S21 are changed by adjusting the speed of the conveyor 223, the supplying speed at which the fiber bundles f' are supplied to the cutting, unit 213 and the cutting speed of the cutting machine 213A are also adjusted accordingly.

The inclination angle α with respect to the horizontal direction of the rods 240 also influences the fiber orientation state of the fiber bundle group F2. For this reason, it is preferable that, in the control step, the fiber orientation state of the plurality of fiber bundles f the fiber bundle group F2 is controlled by changing the inclination angle α with respect to the horizontal direction of the plurality of rods 240 on the basis of the inspection result of the inspecting step. In addition, the frequency of the rods 240 also influences the fiber state of the fiber bundle group F2. For this reason, it is preferable that, in the control step, the fiber orientation state of the plurality of fiber bundles f in the fiber bundle group F2 is controlled by changing the frequency of the plurality of rods 240 on the basis of the inspection result of the inspecting step.

The only one of the control of the fiber orientation state by changing the conveying speed of the first sheet S21 and the running speed of the paste P21 on the first sheet S21, the control of the fiber orientation state by changing the inclination angle α of the rods 240 with respect to the horizontal direction, and the control of the fiber orientation state by changing the vibration frequency of 240 may be performed, or two or more thereof may be combined.

In the related art, there is known a method of evaluating a fiber direction of an anisotropic fiber sheet when laminating a plurality of sheet-shaped anisotropic fiber sheets which do not contain resin and have directionality in the fiber. Specifically, JP 2007-187545 A discloses a method of capturing a moving picture of a sheet surface while irradiating the sheet surface with light from a light source moving relative to the anisotropic fiber sheet and determining a fiber orientation direction from a locus along which a bright portion due to the light reflected on the fiber on the sheet surface is moved.

However, even if the above-described method is applied to a fiber-reinforced resin material such as an SMC after production, since the resin is impregnated, the light reflected on the fiber cannot be sufficiently obtained, and it is difficult to determine the fiber orientation state from the locus of the bright portion. In addition, although it may be conceivable to inspect the fiber orientation state of the fiber bundle group on the production line of the fiber-reinforced resin material by using the above-described method, but it is difficult to inspect the fiber orientation state of the fiber bundle group on the production line for continuously manufacturing the fiber-reinforced resin material. Specifically, on the production line of the fiber-reinforced resin material, since the fiber bundle group runs together with the first sheet and the resin (paste), the locus of the bright portion due to the reflected light in each fiber bundle is not aligned with the orientation direction of the fiber bundle. In addition, since the fiber bundle group in the fiber-reinforced resin material is formed by the cut fiber bundles with a short fiber length, the moving distance of the bright portion in each fiber bundle becomes short. From these facts, it is difficult to inspect the fiber orientation state of the fiber bundle group from the locus of the bright portion on the production line of the fiber-reinforced resin material.

On the other hand, according to the method for manufacturing a fiber-reinforced resin material according to the second embodiment, the fiber orientation state of the fiber bundle group on the production line can be inspected, and the fiber orientation state in the fiber-reinforced resin material can be easily determined. In addition, it is possible to manufacture the fiber-reinforced resin material by changing the manufacturing conditions according to the inspection result and controlling the fiber orientation state of the fiber bundle group.

The method for manufacturing a fiber-reinforced resin material according to the invention is not limited to the method using the manufacturing device 21 described above. For example, a manufacturing method using an inspection device other than the inspection device 2100 may be employed. In addition, even in the case where the operator manually controls the manufacturing conditions by checking the inspection result, the method for manufacturing a fiber-reinforced resin material according to the invention may be a method using the manufacturing device not equipped with the control means.

The method for manufacturing a fiber-reinforced resin material having an inspecting step may be a method in which the scattering step is a step of dispersing and scattering a gas such as air on fiber bundles that are cat and dropped. In addition, a method for manufacturing a fiber-reinforced resin material having an inspecting step may be a method for manufacturing a fiber-reinforced resin material to be used for a stampable sheet by using a thermoplastic resin instead of a thermosetting resin.

[Fiber-Reinforced Resin Material]

Next as a fiber-reinforced resin material according to one embodiment of the invention, a fiber-reinforced resin material manufactured by the above-described method for manufacturing a fiber-reinforced resin material will be specifically described.

The fiber-reinforced resin material according to one embodiment of the invention is a sheet-shaped fiber-reinforced resin material impregnated with a resin between dispersed fiber bundles, diffracted X rays at a diffraction angle 2θ of 25.4° are detected by an X-ray diffraction method, and the roughness β obtained by the following Mathematical Formulas (1) to (3) is in a range of 0.5 to 4.5.

[Mathematical Formula 4]

$$\beta = \int_0^{360} |f(\phi)| d\phi \times \frac{1}{360} = \left( \sum_{i=2}^{N} (|f(\phi_i)| + |f(\phi_{i-1})|) \times d\phi \times \frac{1}{2} \right) \times \frac{1}{360} \quad (1)$$

In the above Mathematical Formula, $f(\phi_i)$ is a luminance obtained by subtracting the average luminance from the luminance $(I(\phi_i))$ at an i-th rotation angle $(\phi_i)$ in the X-ray diffraction measurement represented by the following Mathematical Formula (2), and $d\phi$ is the step width of the X-ray diffraction measurement. $I(\phi_i)$ is normalized so that the integration strength represented by the following Mathematical Formula (3) becomes 10000.

[Mathematical Formula 5]

$$f(\phi_i) = I(\phi_i) - \frac{\sum_{i=1}^{N} I(\phi_i)}{N} \quad (2)$$

$$\int_0^{360} I(\phi) d\phi = \sum_{i=2}^{N} (I(\phi_i) + I(\phi_{i-1})) \times d\phi \times \frac{1}{2} = 10000 \quad (3)$$

The roughness β is a value obtained from a profile derived from fiber orientation in X-ray diffraction measurement of the fiber-reinforced resin material and is measured by the following method.

In the sheet-shaped fiber-reinforced resin material where two sheet samples obtained by cutting the fiber-reinforced resin material which is continuous in the longitudinal direction in the width direction are overlaid in such a manner that the longitudinal directions of the two samples are the same, 25 test pieces having a size of 15 mm in length×15 rum width at equal intervals (N=25) are cut from a range of 300 mm in length×300 mm in width. By using an X-ray apparatus, the test piece was rotated about the thickness direction thereof while the test piece was irradiated with X-rays by a transmission method, and a diffracted X ray is detected by a detector arranged at a diffraction angle 2θ=25.4°, so that the luminance $(I(\phi_i))$ at an i-th rotation angle $(\phi_i)$ is measured. However, $I(\phi_i)$ is assumed to be normalized so that the integration strength represented by Mathematical Formula (3) becomes 10000.

Then, as represented by Mathematical Formula (2), the luminance $f(\phi_i)$ obtained by subtracting the average luminance from the luminance $(I(\phi_i))$ is defined, the roughness for each of the 25 test pieces is obtained from Mathematical Formula (1) derived using the luminance $f(\phi_i)$, and the average value thereof is defined as the roughness β.

The roughness β indicates that, as the roughness becomes close to zero, the orientation of the fiber bundle becomes less disturbed.

If the roughness β is equal to or larger than 0.5, the uniformity of orientation of the fiber bundle is not to be too high, and thus, it is possible to prevent the formability from being deteriorated due to impairment of the flowability of the resin at the time of being molding-processed as an SMC or a stampable sheet. In addition, it is unnecessary to excessively lower the speed of the production line of the fiber-reinforced resin material, and it is possible to secure sufficient productivity. The roughness β is preferably equal to or larger than 1.0, more preferably equal to or larger than 1.5, further preferably equal to or larger 2.0, particularly preferably equal to or larger than 2.5.

If the roughness β is equal to or smaller than 4.5, it is possible to prevent the anisotropy (for example, the bending modulus of elasticity in the longitudinal direction and the width direction) of the physical properties at each part of the molded article obtained by molding the sheet-shaped fiber-reinforced resin material from being too high. The roughness β is preferably equal to or smaller than 4.0, more preferably equal to or smaller than 3.5.

The fiber-reinforced resin material according to one embodiment of the invention is a sheet-shaped fiber-reinforced resin material impregnated with a resin between dispersed fiber bundles, and when the longitudinal direction of the fiber-reinforced resin material is set to 0° direction and the width direction is to set to 90°, a diffracted X-ray with a diffraction angle 2θ of 25.4° is detected by an X-ray diffraction method, the sum of the average value and the standard deviation of the degree of crystal orientation $f_a$ of the fiber bundle based on the 0° direction obtained by the following Mathematical Formulas (4) to (6) is in a range of 0.05 to 0.13.

[Mathematical Formula 6]

$$f_a = 2a - 1 \quad (4)$$

$$a = \frac{\sum_{i=1}^{N} I(\phi_i) \cos^2 \phi_i}{\sum_{i=1}^{N} I(\phi_i)} \quad (5)$$

$$\int_0^{360} I(\phi) d\phi = \sum_{i=2}^{N} (I(\phi_i) + I(\phi_{i-1})) \times d\phi \times \frac{1}{2} = 10000 \quad (6)$$

In Mathematical Formula (4), "a" is the orientation coefficient represented by Mathematical Formula (5). $I(\phi_i)$ is the luminance at the i-th rotation angle $(\phi_i)$ in the X-ray diffraction measurement and is normalized so that the integration strength represented by Mathematical Formula (6) becomes 10000.

The degree of crystal orientation of the fiber bundle is a value obtained from the degree of crystal orientation calculated from the diffraction image generated by irradiating the fiber-reinforced resin material with X rays and is measured by the following method.

Similarly to the measurement method for the roughness β, 25 test pieces are cut out from the sheet-shaped fiber-reinforced resin material (N=25), and by using an X-ray apparatus, a diffracted X-ray with a diffraction angle 2θ=25.4° is obtained, so that the luminance $(I(\phi_i))$ at an i-th rotation angle $(\phi_i)$ is measured. However, $I(\phi_i)$ is assumed to be normalized so that the integration strength represented by Mathematical Formula (6) becomes 10000. Next, by using the measured $I(\phi_i)$, the orientation coefficient "a" for each of the 25 test pieces is obtained by Mathematical Formula (5). In addition, by using the obtained orientation coefficient "a", the degree of crystal orientation $f_a$ for each of the 25 test pieces is obtained by Mathematical Formula (4), and the average value and standard deviation thereof are calculated.

If the sum of the average value and the standard deviation of the degree of crystal orientation $f_a$ of the fiber bundle is equal to or larger than 0.05, the uniformity of the orientation of the fiber bundle is not to be too high, and thus, it is possible to prevent the formability from being deteriorated due to impairment of the flowability of the resin at the time of being molding-processed as an SMC or a stampable sheet. In addition, it is unnecessary to excessively lower the speed of the production line of the fiber-reinforced resin material, and it is possible to secure sufficient productivity.

The sum of the average value and the standard deviation of the degree of crystal orientation $f_a$ of the fiber bundle is preferably equal to or larger than 0.06, more preferably equal to or larger than 0.08.

If the sum of the average value and the standard deviation of the degree of crystal orientation $f_a$ of the fiber bundle is equal to smaller than 0.13, it is possible to suppress the irregularity (CV value) of the physical properties between the portions in the longitudinal direction and the width direction of the molded article formed with the fiber-reinforced resin material from becoming too large.

The sum of the average value and the standard deviation of the degree of crystal orientation $f_a$ of the fiber bundle is preferably equal to or smaller than 0.12, more preferably equal to or smaller than 0.11.

As described above, with respect to the fiber-reinforced resin material according to the invention, since it is possible to uniformly disperse the cut fiber bundles without directionality by using the above-described method for manufacturing a fiber-reinforced resin material, the strength is maintained to be uniform in all directions. In addition, since the fiber-reinforced resin material according to the invention has excellent resin flowability during molding processing, the fiber-reinforced resin material is excellent in moldability.

[Molded Article]

The molded article according to the invention is a molded article of a sheet-shaped fiber-reinforced resin material in which a resin is impregnated between dispersed fiber bundles. In the molded article according to the invention, when the longitudinal direction of the molded article is set to the 0° direction and the width direction is set to the 90° direction, the ratio (0° bending modulus of elasticity/90° bending modulus of elasticity) of the bending moduli of elasticity [GPa] in the respective directions is in a range of 0.8 to 1.2. In the molded article according to the invention, any one of the coefficients of variation (CV) of the bending moduli of elasticity (CV of 0° bending modulus of elasticity and CV of 90° bending modulus of elasticity) in the respective directions of 0° and 90° [%] is in a range of 5 to 15.

The ratio (0° bending modulus of elasticity/90° bending modulus of elasticity) is a value indicating the uniformity of the orientation direction of the fiber bundle in the molded article. The ratio (0° bending modulus of elasticity/90° bending modulus of elasticity) is in a range of 0.8 to 1.2, preferably in a range of 0.9 to 1.1, more preferably in a range of 0.95 to 1.05. If the ratio (0° bending modulus of elasticity/90° bending modulus of elasticity) is within the above-described range, the anisotropy of the physical properties of the molded article is sufficiently low, and thus, there is no practical problem.

The coefficient of variation (CV) of the 0° bending modulus of elasticity is in a range of 5 to 15, preferably in a range of 5 to 12, more preferably in a range of 7 to 9. If the coefficient of variation (CV) of the 0° bending modulus of elasticity is equal to or larger than the lower limit value, the uniformity of orientation of the fiber bundle becomes too high, and the flowability of the resin at the time of molding processing as or a SMC or a stampable sheet is impaired, so that it is possible to suppress deterioration of moldability. In addition, it is unnecessary to excessively lower the speed of the production line of the fiber-reinforced resin material, and it is possible to secure sufficient productivity. If the coefficient of variation (CV) of the 0° bending modulus of elasticity is equal to or smaller than the upper limit value, the irregularity (CV value) of the physical properties between the portions in the longitudinal direction of the molded article is sufficiently small.

The coefficient of variation (CV) of the 90° bending modulus of elasticity is in a range of 5 to 15, preferably in a range of 5 to 12, more preferably in a range of 7 to 9 for the same reason as the coefficient of variation (CV) of 0° bending modulus of elasticity. If the variation coefficient (CV) of the 90° bending modulus of elasticity is equal to or smaller than the upper limit value, the irregularity (CV value) of the physical properties between the portions in the width direction of the molded article is sufficiently small.

Hereinafter, the invention will be specifically described with reference to examples. However, the invention is not limited to the following examples, but appropriate changes are available within the scope without changing the spirit thereof.

Example 1

In Example 1, by using the manufacturing device 11 illustrated in FIG. 1, with respect to the surface of the first sheet S11 where the interval D between the adjacent rods 140 is changed, the difference (0° to 90°) was measured between the number of fiber bundles CF deposited along the conveying direction (set to 0° direction) of the first sheet S11 and the number of fiber bundles CF deposited along the width direction (set to 99° direction) of the first sheet S11. As the absolute value of this difference is smaller, it can be determined that the fiber bundles CF can be uniformly dispersed without directionality. In addition, the conveying speed of the first sheet S11 in this example was set to 5 m/min.

Figure 17:
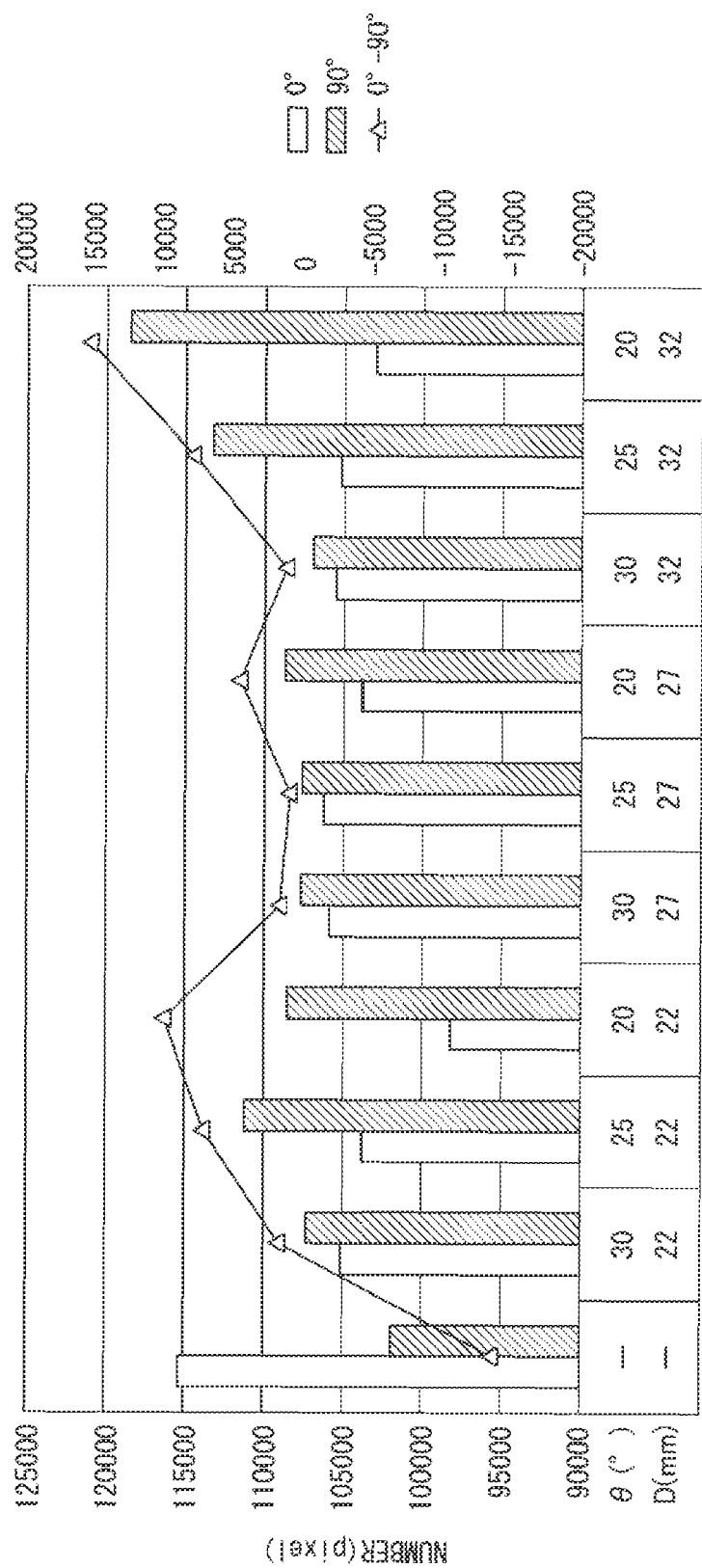
FIG. 17 is a graph illustrating measurement results in Example 1.

In addition, the inclination angle $\theta_A$ of the rod 140 was chanced, and the measurement was performed. Table 1 lists a summary of the measurement results. In addition, a graph of the measurement results illustrated in Table 1 is illustrated in FIG. 17.

TABLE 1

| D | mm | — | 22 | 22 | 22 | 27 | 27 | 27 | 32 | 32 | 32 |
|---|---|---|---|---|---|---|---|---|---|---|---|
| $\theta_A$ | ° | — | 30 | 25 | 20 | 30 | 25 | 20 | 30 | 25 | 20 |
| 0° | pixel | 115698 | 105484 | 103964 | 98437.1 | 106109 | 106531 | 104140 | 105739 | 105387 | 103257 |
| 90° | pixel | 102100 | 107624 | 111530 | 108778 | 107931 | 107773 | 108858 | 107113 | 113509 | 118850 |
| 0°-90° | pixel | −13598 | 2140.87 | 7565.79 | 10340.5 | 1822.07 | 1241.21 | 4717.69 | 1374.71 | 8122.43 | 15593.1 |

In addition, in this measurement, the average value of the fiber lengths of the fiber bundles CF was 25.4 mm. In this measurement, the fiber bundles CF deposited on the surface of the first sheet S11 was imaged the fiber bundles CF deposited along the conveying direction (0° direction) of the first sheet S11 and the fiber bundles CF deposited in the width direction (90° direction) of the first sheet S11 were extracted from the obtained image, and the respective numbers (pixels) were counted. In addition, in this measurement, as a comparative example, the same measurement was performed also in the case where the rods 140 were not arranged. In addition, the measurement results are illustrated in Table 1 and the left side of FIG. 17.

As illustrated in Table 1 and FIG. 17, by arranging the plurality of rods 140 under the cutting machine 113A and adjusting the interval D and the inclination angle $\theta_A$, the ratio of the fiber bundles CF deposited along the conveying direction of the first sheet S11 (0° direction) of the first sheet S11 and the fiber bundles CF deposited along the width direction (90° direction) of the first sheet S11 can be changed.

It can be understood that, depending on the interval D between the rods 140 and the inclination angle $\theta_A$, the proportion of the fiber bundles CF deposited along the width direction (90°) of the first sheet S11 is increased in comparison with the proportion of the fiber bundles CF deposited along the conveying direction (0° direction) of the first sheet S11. In this case, it is possible to increase the proportion of the fiber bundles CF deposited along the conveying direction (0° direction) of the first sheet S11 by increasing the conveying speed of the above-described first sheet S11.

Therefore, by adjusting the conveying speed of the first sheet S11 in addition to the interval D of the rods 140 and the inclination angle $\theta_A$, it is possible to change the ratio between the fiber bundles CF deposited along the conveying direction (0° direction) of the first sheet S11 and the fiber bundles CF deposited along the width direction (90° direction) of the first sheet S11.

Example 2

In Example 2, an SMC was manufactured in the same manner as Example 1 except that the manufacturing device 11 illustrated in FIG. 1 is used to change the conditions such as the interval D between the adjacent rods 140 to the conditions illustrated in the following Table 2. In addition, in this example, the conveying speed of the first sheet S11 was set to 5 m/min.

As the fiber bundle CF, a carbon fiber (product name: TR50S15L) produced by Mitsubishi Rayon Co., Ltd. was used. A paste P1 was prepared as follows.

With respect to 100 parts by mass of epoxy acrylate resin as a thermosetting resin (product name: Neopol 8051, produced by Nippon Yupika), 0.5 parts by mass of a 75% solution of 1,1-di(t-butylperoxy) cyclohexane (product name: Perhexa C-75 (EB), produced by NOF CORPORATION) and 0.5 parts by mass of a 74% solution of t-butyl peroxyisopropyl carbonate (product name Kayacarbon BIC-75, produced by Kayaku Akzo Co. Ltd.) were added as a curing agent 0.35 parts by mass of a phosphoric acid ester-based derivative composition (product name: MOLD WIZ INT-EQ-6, produced by Axel Plastic Research Laboratory Co., Ltd.) was added as an internal mold releasing agent, 15.5 parts by mass of modified diphenylmethane diisocyanate (product name: Cosmonate LL, produced by Mitsui Chemicals, Inc.) was added as a viscous agent, 0.02 parts by mass of 1,4-benzoquinone was added as a stabilizing agent, 5 parts by mass of milled carbon fiber (trade name: MP30X, weight average fiber length being 95 μm, content of fiber of 350 μm or less being 99% by mass produced by Nippon Polymer Industry Co. Ltd.) were added, and these were sufficiently mixed and stirred to obtain the paste P1.

Then, the molded plate obtained by molding the manufactured SMC (content of the fiber bundle CF: 49% by mass) was evaluated for the strength (bending strength, bending modulus of elasticity).

Specifically, in the evaluation test, first the SMCs were manufactured for the case where the rods 140 were not arranged (Comparative Example 1), the case where the interval D between the rods 140 was 32 mm and the inclination angle $\theta_A$ was 15° (Example 1), and the case where the interval D between the rods 140 was 3 mm and the inclination angle $\theta_A$ was 25° (Example 2).

Next, after the SMC was cured for one week at a temperature of 25±5° C. after manufacturing of the SMC, in a panel forming mold (300 mm×300 mm×2 mm, surface chrome plating finishing) having a fitting portion at the end, the SMC was cut in unit of 230 mm×230 mm, the conveying directions (MD directions) of the SMC in the SMC manufacturing device were aligned, and two sheets thereof were placed into the center of the mold. Then, the SMC was heated and pressed in the mold under the conditions of 140° C., 8 MPa, and 5 minutes, so that the SMC molded plate was obtained. In addition, two sheets of SMC having a weight of about 150 g of two SMCs were laminated in the same direction to have a weight of about 300 g.

Figure 19:
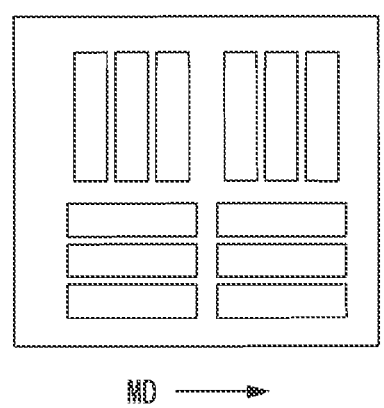
FIG. 19 is a plan view illustrating an arrangement of test pieces cut out from molded articles of SMC in Example 2.

Next, in order to measure the bending strength and the bending modulus of elasticity of the SMC molded plate, in accordance with the arrangement illustrated in FIG. 19, six test pieces each having a length of 110 mm and a width of 25 mm were cut out from the SMC molded plate along the SMC conveying direction (0° direction) and the SMC width direction (90° direction). Then, by using a 5 kN Instron universal testing machine, a three-point bending test was performed on each test piece at L/D=40 and a crosshead speed of 5 mm min, and the bending strength and bending modulus of elasticity of each test piece were measured, and the respective average values thereof was obtained. In addition, the difference (0°-90°) and the ratio (0°/90°) were calculated. Table 2 lists a summary of the evaluation results. In addition, a graph of the measurement results illustrated in Table 2 is illustrated in Fig.

TABLE 2

| | Unit | Comparative Example 1 | Example 1 | Example 2 |
|---|---|---|---|---|
| D | mm | — | 32 | 32 |
| $\theta_A$ | ° | — | 15 | 25 |
| 0° bending modulus of elasticity ① | GPa | 24.1 | 21.5 | 23.5 |
| 0° bending strength ③ | MPa | 288.6 | 261.9 | 316.0 |
| 90° bending modulus of elasticity ② | GPa | 20.0 | 20.4 | 24.2 |

TABLE 2-continued

| | Unit | Comparative Example 1 | Example 1 | Example 2 |
|---|---|---|---|---|
| 90° bending strength ④ | MPa | 271.6 | 295.0 | 323.9 |
| ①−② | — | 4.1 | 1.1 | −0.7 |
| ①/② | — | 1.21 | 1.05 | 0.97 |

Figure 18:
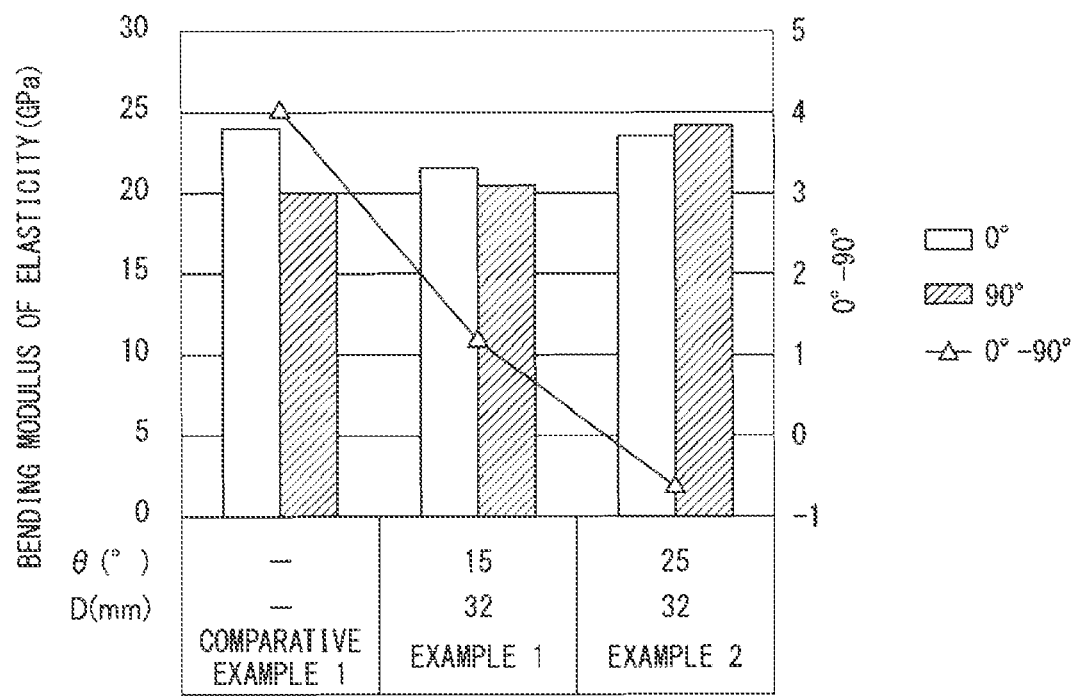
FIG. 18 is a graph illustrating measurement results in Example 2.

As illustrated in Table 2 and FIG. 18, in the case where the rods 140 are arranged, it is understood that the directionality of the strength (bending strength, bending modulus of elasticity) of the manufactured SMC is smaller than the case where the rods 140 are not arranged. It can be clarified From these facts that, in the case where the rods 140 are arranged, it is possible to uniformly disperse the fiber bundles without directionality.

Example 3

In Example 3, in the SMC manufacturing device, the interval D of the rods 140 was set to 32 mm, the angle $\theta_A$ of the rods 140 was set to 25°, the conveying speed of the first sheet S11 was set to 3 m/min, and the SMC (content of the fiber bundle CF being 53% by mass) was prepared in the same manner as in Example 2 except that the milled carbon fiber was not added.

using the SMC, a SMC molded plate was obtained in the same manner as in Example 2. Bending test pieces were cut out in the same manner as in Example 2, and a bending test was performed in the same manner as in Example 2. However, the test conditions in Example 3 are as illustrated in the following Table 3.

TABLE 3

| | Item | Example 2 Bending Test | Example 3 Bending Test |
|---|---|---|---|
| Shape of Test Piece | Thickness | 2ply Laminated (2.1 mm) | 2ply Laminated (2.1 mm) |
| | Width | 25 mm | 25 mm |
| | Length | 110 mm | 60 mm |
| Test Condition | Pressed Surface | Non-Knock-Pin Surface | Non-Knock-Pin Surface |
| | Inter-Point Distance | 40 Times Average Thickness | 16 Times Average Thickness |
| | Indenter Radius | R5 | R5 |
| | Point Radium | R3.2 | R3.2 |
| | Test Speed | 5 mm/min | 2.6 mm./min |
| | Number of Times of Measurement | Conveying Direction 6/Width Direction 6 | Each 6 |
| | Cushion Material | Teflon Film 3 Sheets (Nittoflon Film Product No.) | Teflon Film 4 Sheets |

Figure 20A:
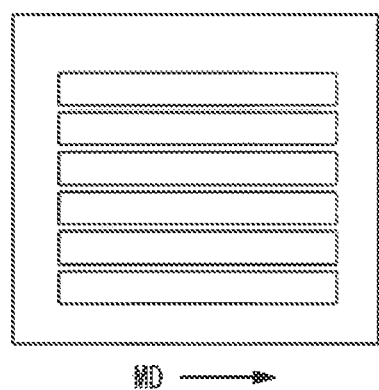
FIG. 20A is a plan view illustrating an arrangement of test pieces cut out from molded articles of SMC in Example 3.
Figure 20B:
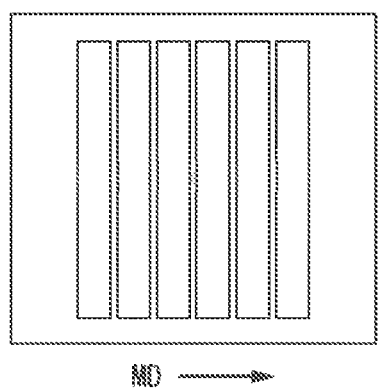
FIG. 20B is a plan view illustrating an arrangement of test pieces cut out from molded articles of SMC in Example 3.
Figure 21:
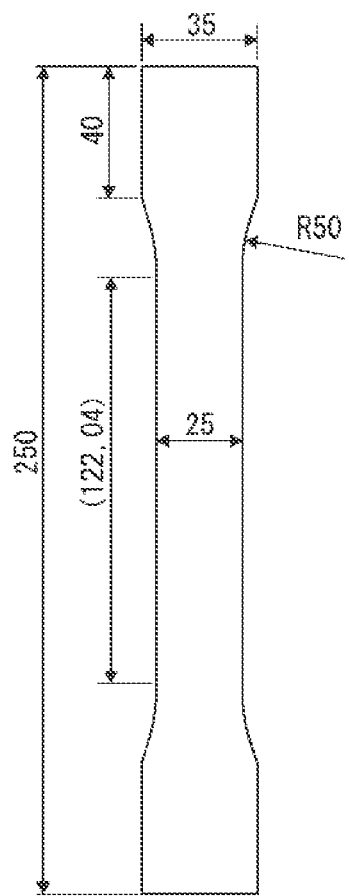
FIG. 21 is a plan view illustrating a test piece used in a tensile test in Example 3.

In addition, in order to measure the tensile strength and the tensile modulus of elasticity of the SMC molded plate, in accordance with the arrangement illustrated in FIG. 20A and FIG. 20B, six test pieces illustrated in FIG. 21 were cut out from the SMC molded plate along the SMC conveying direction (0° direction) and width direction (90° direction). Then, by using a 100 kN Instron universal testing machine, a tensile test was carried out under the test conditions in Table 4 below.

TABLE 4

| | Item | 0° Tensile · 90° Tensile |
|---|---|---|
| Shape of Test Piece | Thickness | 2ply Laminated (2.1 mm) |
| | Width | 25 mm |
| | Length | 250 mm |
| | Shape | Dumbbell |

TABLE 4-continued

| | Item | 0° Tensile · 90° Tensile |
|---|---|---|
| Test Condition | Distortion Gauge | Single Axis 20 mm |
| | Test Speed | 2.6 mm./min |
| | Number of Times of Measurement | Each 6 |

The summary of the obtained evaluation results is listed in Table 5 and Table 6 as follow. In addition, with respect to the test in the direction of 90°, the measurement temperature was changed and was illustrated in the same tables.

TABLE 5

| | Example 3 Bending Test | | | | |
|---|---|---|---|---|---|
| Measurement Angle | 90° | 0° | 90° | 90° | 90° |
| Measurement Temperature (° C.) | −40 | 23 | 23 | 90 | 120 |
| Strength (MPa) 1 | 409 | 526 | 324 | 433 | 252 |
| 2 | 506 | 526 | 350 | 402 | 210 |
| 3 | 353 | 426 | 461 | 277 | 252 |
| 4 | 425 | 286 | 500 | 387 | 295 |
| 5 | 447 | 483 | 447 | 408 | 256 |

TABLE 5-continued

| | Example 3 Bending Test | | | | |
|---|---|---|---|---|---|
| 6 | 314 | 323 | 463 | 393 | 219 |
| Average | 409 | 428 | 424 | 383 | 247 |
| Standard Deviation | 68.2 | 103.4 | 70.2 | 54.5 | 30.3 |
| CV (%) | 17% | 24% | 17% | 14% | 12% |
| max | 506 | 526 | 500 | 433 | 295 |
| Difference | 97 | 98 | 76 | 50 | 48 |
| min | 314 | 286 | 324 | 277 | 210 |
| Difference | 95 | 142 | 100 | 106 | 37 |
| Modulus of Elasticity (GPa) 1 | 22.3 | 23.5 | 17.1 | 21.0 | 16.3 |
| 2 | 22.1 | 23.2 | 21.1 | 19.1 | 12.4 |
| 3 | 21.5 | 17.9 | 22.2 | 16.3 | 15.2 |
| 4 | 24.7 | 21.8 | 21.7 | 19.7 | 17.5 |
| 5 | 22.9 | 21.8 | 23.0 | 22.3 | 16.4 |
| 6 | 21.3 | 18.8 | 21.3 | 22.2 | 13.7 |
| Average | 22.5 | 21.2 | 21.1 | 20.1 | 15.3 |

TABLE 5-continued

Example 3 Bending Test

| | | | | | | |
|---|---|---|---|---|---|---|
| | Standard Deviation | 1.24 | 2.31 | 2.06 | 2.27 | 1.90 |
| | CV (%) | 5% | 11% | 10% | 11% | 12% |
| | max | 24.7 | 23.5 | 23.0 | 22.3 | 17.5 |
| | Difference | 2.2 | 2.3 | 1.9 | 2.2 | 2.3 |
| | min | 21.3 | 17.9 | 17.1 | 16.3 | 12.4 |
| | Difference | 1.2 | 3.3 | 4.0 | 3.8 | 2.9 |

TABLE 6

Example 3 Tensile Test

| | | | | | | |
|---|---|---|---|---|---|---|
| Measurement Angle | | 90° | 0° | 90° | 90° | 90° |
| Measurement Temperature (° C.) | | −40 | 23 | 23 | 90 | 120 |
| Strength (MPa) | 1 | 193 | 134 | 131 | 152 | 129 |
| | 2 | 151 | 193 | 158 | 117 | 109 |
| | 3 | 119 | 147 | 175 | 142 | 98 |
| | 4 | 214 | 195 | 180 | 105 | 63 |
| | 5 | 169 | 182 | 140 | 150 | 92 |
| | 6 | 159 | 131 | 173 | 119 | 143 |
| | Average | 168 | 164 | 160 | 131 | 106 |
| | Standard Deviation | 33.2 | 29.7 | 20.2 | 19.7 | 28.2 |
| | CV (%) | 20% | 18% | 13% | 15% | 27% |
| | max | 214 | 195 | 180 | 152 | 143 |
| | Difference | 47 | 31 | 21 | 21 | 37 |
| | min | 119 | 131 | 131 | 105 | 63 |
| | Difference | 49 | 33 | 29 | 26 | 43 |
| Modulus of Elasticity (GPa) | 1 | 34.7 | 27.3 | 27.2 | 27.6 | 24.6 |
| | 2 | 28.1 | 25.4 | 29.8 | 32.2 | 30.6 |
| | 3 | 25.0 | 35.2 | 30.1 | 32.3 | 26.3 |
| | 4 | 33.6 | 31.4 | 32.9 | 20.4 | 24.6 |
| | 5 | 33.4 | 27.5 | 28.6 | 33.8 | 25.6 |
| | 6 | 31.2 | 37.7 | 26.7 | 30.8 | 33.4 |
| | Average | 31.0 | 30.8 | 29.2 | 29.5 | 27.5 |
| | Standard Deviation | 3.76 | 4.89 | 2.26 | 4.93 | 3.64 |
| | CV (%) | 12% | 16% | 8% | 17% | 13% |
| | max | 34.7 | 37.7 | 32.9 | 33.8 | 33.4 |
| | Difference | 3.7 | 7.0 | 3.7 | 4.3 | 5.9 |
| | min | 25.0 | 25.4 | 26.7 | 20.4 | 24.6 |
| | Difference | 6.0 | 5.4 | 2.5 | 9.1 | 2.9 |

The standard deviation and the CV (coefficient of variation) in Table 5 and Table 6 were calculated by using the following Mathematical Formula.

[Mathematical Formula 7]

Standard Deviation CV (Coefficient of Variation)

$$\bar{x} = \left(\sum_{i=1}^{n} x_i\right)/n$$

$$s_{n-1} = \sqrt{\left(\sum_{i=1}^{n} x_i^2 - n\bar{x}^2\right)/(n-1)}$$

$$CV = 100 \times s_{n-1}/\bar{x}$$

where:
$\bar{x}$=sample mean (average):
$v_n$=sample standard deviation:
CT=sample coefficient of variation in percent:
n=number of specimens: and
$x_i$=measured of derived property.

As illustrated in Tables 5 and 6, it is clarified that, when the longitudinal direction of the SMC is set to the 0° direction and the width direction is set to the 90° direction, in the SMC of which the ratio (0° bending modulus of elasticity/90° bending modulus of elasticity) of the bending moduli of elasticity [GPa] in the respective directions is in a range of 0.8 to 1.2 and any one of the coefficients of variation (CV) of the bending moduli of elasticity (the CV [%] of the 0° bending modulus of elasticity and the CV [%] of the 90° bending modulus of elasticity) is in a range of 5 to 15, the directionality of the strength (bending strength, bending modulus of elasticity) is small, and the strength can be maintained to be more uniform in all directions. Namely, as illustrated in Example 3, the SMC was excellent in the flowability of the resin at the time of a molding process, and the anisotropy and the irregularity of the physical properties of the molded article were reduced.

Experimental Example A1

As the first light irradiation means and the second light irradiation means, bar-shaped LED lights (White Bar 132-15, Light: CA-DBW13, Diffusion Plate: OP-42282, produced by Keyence Corporation) were prepared. As the imaging means, a digital double speed monochrome camera (XG-035M, produced by Keyence Corporation) and a high resolution/low distortion lens 16 mm (CA-LH 16) were prepared. As the orientation determination means, a high-speed and flexible image processing system (Controller XG-7000, Illumination Extension Unit: CA-DC 21E, produced by Keyence Corporation) was prepared.

A carbon fiber bundle (trade name "TR50S15L", produced by Mitsubishi Rayon Co., Ltd.) was cut so that the average fiber length was 25.4 mm, a plurality of carbon fiber bundles were arranged so that the fiber axis direction was aligned in one direction, and a sheet-shaped test fiber bundle group having a rectangular shape of 100 mm (length)×100 mm (width) as viewed in a plan view was manufactured. A pair of first light irradiation means and a pair of second light irradiation means were arranged around the test fiber bundle group so that the test fiber bundle group was irradiated with light obliquely from the upper side at an angle of 45°. At this time, the longitudinal direction of the pair of first light irradiation means and the fiber axis direction of the fiber bundle in the test fiber bundle group were set to be parallel to each other, and the longitudinal direction of the pair of second light irradiation means and the fiber axis direction of the fiber bundle in the test fiber bundle group were set to be perpendicular to each other. The fiber axis direction of the fiber bundle in the test fiber bundle group in this state was set to 0°.

Figure 22:
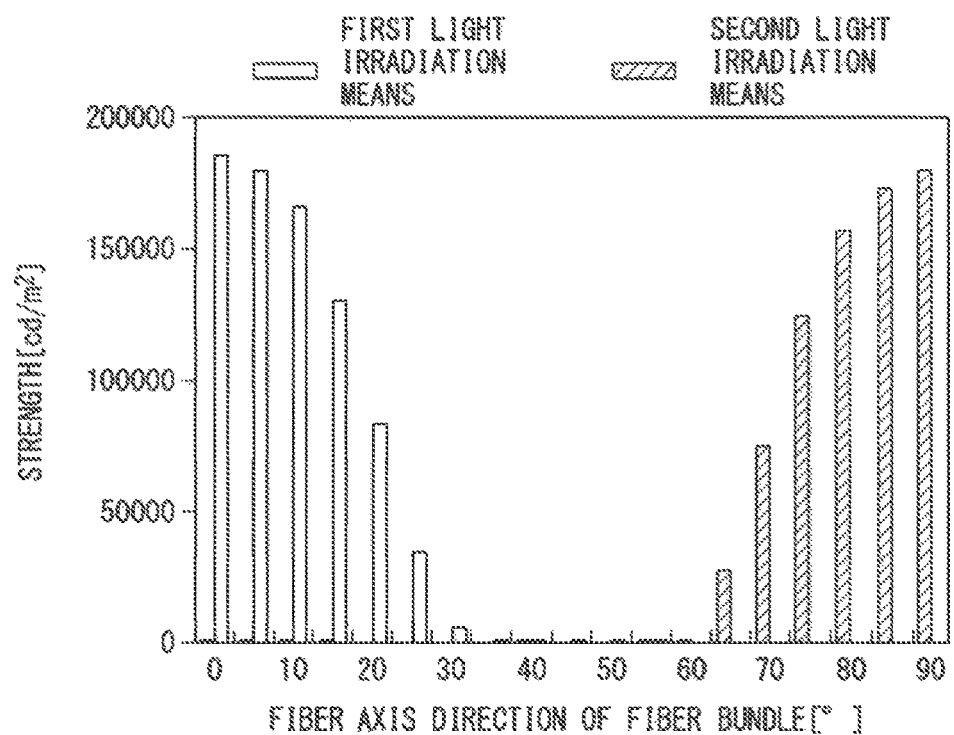
FIG. 22 is a graph illustrating a relationship between an angle of a fiber axis of a fiber bundle and luminance in Experimental Example A1.

The imaging means was installed above the center of the test fiber bundle group. The still image of the upper surface of the test fiber bundle group was captured by the imaging means while the test fiber bundle group was irradiated with light by the first light irradiation means, and the orientation determination means measured the luminance on the upper surface of the test fiber bundle group. Subsequently, the test fiber bundle group was rotated by 90° in increment of 5°, the still image in the state of being irradiated with light by the first light irradiation means in the fiber axis direction of the fiber bundle at each angle was similarly captured, and the luminance was measured. Next the irradiation of the light by the first light irradiation means was stopped, the test fiber bundle group was irradiated with light by the second light irradiation means, and the luminance of the upper surface of the test fiber bundle group of which the fiber axis direction of the fiber handles is 99° was measured. Subsequently, the test fiber bundle group was rotated to 0° in increments of 5°, the still image in the state of being irradiated with light by the second light irradiation means in the fiber axis direction of the fiber bundle at each angle was similarly captured, and the luminance was measured. FIG. 22 illustrates the measurement results of the luminance in the test fiber bundle group in the fiber axis direction of the fiber bundle of each angle.

As illustrated in FIG. 22, in the irradiation of the light by the first light irradiation means for irradiating light obliquely from the upper side in a direction perpendicular to the fiber bundle of which the fiber axis direction was 0° as viewed in a plan view, as the fiber bundle in the fiber axis direction was closer to 0°, the area of the bright portion due to the reflected light was increased in the test fiber bundle group in the still image, and the luminance was increased. On the other hand, in the irradiation of the light by the second light irradiation means for irradiating light obliquely from the upper side in a direction perpendicular to the fiber bundle of which the fiber axis direction was 90° as viewed in a plan view, as the fiber axis direction of the fiber bundle is close to 90°, the area of the bright portion due to the reflected light was increased in the test fiber bundle group in the still image, and the luminance was increased. In addition, when the fiber axis direction of the fiber bundle was in a range of 30 to 60°, the luminance was extremely small with respect to any light irradiation of the first light irradiation means and the second light irradiation means.

Example A1

A fiber reinforced resin material was manufactured by the manufacturing device 21 exemplified in FIG. 15. As the elongated fiber bundle f', a carbon fiber bundle (trade name "TR50S15L", produced by Mitsubishi Rayon Co., Ltd.) was used. A paste P21 was prepared as follows. With respect to 100 parts by mass of epoxy acrylate resin as a thermosetting, resin (product name: Neopol 8051, produced by Nippon Yupika), 0.5 parts by mass of a 75% solution of 1,1-di(t-butylperoxy) cyclohexane (product name: Perhexa C-75 (EB), produced by NOF CORPORATION) and 0.5 parts by mass of a 74% solution of t-butyl peroxyisopronyl carbonate (product name: Kayacarbon BJC-75, produced by Kayaku Akio Co., Ltd.) were added as a curing agent, 0.35 parts by mass of a phosphoric acid ester-based derivative composition (product name: MOLD WIZ INT-EQ-6, produced by Axel Plastic Research Laboratory Co., Ltd.) was added as an internal mold releasing agent, 15.5 parts by mass of modified diphenylmethane diisocyanate (product name: Cosmonate LL, produced by Mitsui Chemicals. Inc.) was added as a viscous agent, 0.02 parts by mass of 1,4-benzoquinone was added as a stabilizing agent, 5 parts by mass of milled carbon fiber (trade name: MP30X, weight average fiber length being 95 µm, content of fiber of 350 µm or less being 99% by mass, produced by Nippon Polymer Industry Co., Ltd.) were added, and these were sufficiently mixed and stirred to obtain the paste P21.

In the inspection device 2100, a pair of bar-shaped LED lights (white bar 132-15, light: CA-DBW13, Diffusion Plate: OP-42282, produced by Keyence Corporation) were used. In addition, the same units as the first irradiation unit 2102a and the second irradiation unit 2102b were prepared as the third irradiation unit 2104a and the fourth irradiation unit 2104b of the second light irradiation means 2104. As the imaging means 2106, a digital double-speed monochrome camera (XG-035M, produced by Keyence Corporation) and a high resolution/low distortion lens 16 mm (CA-LH16) were used. As the orientation determination means 2108, a high-speed and flexible image processing system (controller: XG-7000, Illumination Extension Unit: CA-DC 21E, produced by Keyence Corporation) was used. The inclination angle $\phi_1$ of the first irradiation unit 2102a with respect to the horizontal direction, the inclination angle $\phi_2$ of the second irradiation unit 2102b with respect to the horizontal direction, the inclination angle $\theta_1$ of the third irradiation unit 2104a with respect to the horizontal direction, and the inclination angle $\theta_2$ of the fourth irradiation unit 2104b with respect to the horizontal direction were set to 45°.

In manufacturing the fiber-reinforced resin material, a first resin sheet S21 having a thickness of 0.5 mm was formed, and the fiber bundle f' was cut with a cutting machine 213A to drop fiber bundles f' having an average fiber length of 25.4 mm, and a sheet-shaped fiber bundle group F2 having a thickness of 1.0 mm was formed. The conveying speed of the first sheet S21 and the running speed (the speed of the conveyor 223) of the paste P21 applied on the first sheet S21 were 5 m/min. In addition, as the rods 240, the plurality of rods having a diameter of 3.0 mm were arranged side by side in parallel to the conveying direction of the first sheet S21. The interval between adjacent rods 240 was set to 35 mm. The inclination angle α of the rods 240 with respect to the horizontal direction was set to 25°.

Figure 23:
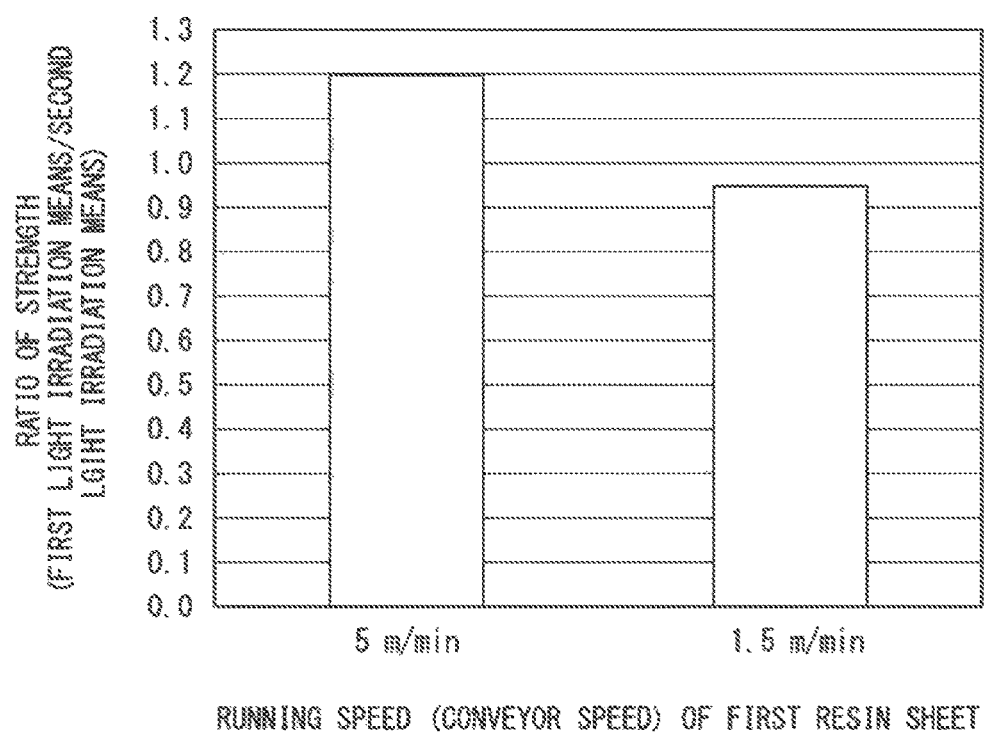
FIG. 23 is a graph illustrating a relationship between a running speed (conveyor speed) of the first resin sheet and a luminance ratio in Example A1.

During manufacturing, in the inspection device 2100, with respect to a rectangular area of 100 mm×100 mm as viewed in a plan view of the upper surface of the fiber bundle group F2, the luminance in the state of being irradiated with light by the first light irradiation means 2102 and the luminance in the state of being irradiated with light by the second light irradiation means 2104 were measured. The luminance ratio of the luminance in the state of being irradiated with light by the first light irradiation means 2102 to the luminance in the state of being irradiated with light by the second light irradiation means 2104 was 1.2. Subsequently, the running speed of the first resin sheet (the speed of the conveyor 223) was reduced to 1.5 m/min and again the luminance ratio was calculated to be 0.95. The results are illustrated in FIG. 23. In addition, the speed at which the fiber bundle f' is supplied to the cutting machine 213A and the cutting speed of the cutting machine 213A were adjusted in accordance with the deceleration of the conveying speed of the first sheet S21 and the running speed of the paste P21 (the speed of the conveyor 23) so that the thickness of the fiber bundle group F2 does not change.

In this manner, by determining the fiber orientation state of the fiber bundle group F2 from the luminance ratio on the production line and changing the conveying speed of the first sheet S21, the fiber bundle group F2 with a more random fiber orientation state was formed.

[Measurement of Roughness β]

The roughness β was measured by the following method.

After the fiber-reinforced resin material (SMC) was cured for one week at a temperature of 25±5° C. after manufacturing, two pieces of the cured SMC were cut out with a rolling cutter in a size of a length of 300 mm and a width of 300 mm, and the two pieces are laminated so that the longitudinal directions of the two pieces of SMC having a weight of about 250 g were the same. Based on the center of the cut material having a weight of about 500 g, 25 test pieces having a size of a length of 15 mm and a width of 15 mm were cut out at intervals of 30 min from the left and right two columns and the upper and lower two columns.

Next, by using an X-ray apparatus, the test piece was rotated about the thickness direction thereof while the test piece was irradiated with X-rays by a transmission method, and a diffracted X-ray was obtained by a detector arranged at a diffraction angle 2θ=25.4°, so that the luminance ($I(\phi_i)$)

at an i-th rotation angle ($\phi_i$) was measured. However, I($\phi_i$) is assumed to be normalized so that the integration strength becomes 10000.

In measuring the roughness β, Empyrean produced by PANalytical Co. was used as an X-ray diffraction apparatus, the tube voltage was set to 45 kV, and the tube current was set to 40 mA. In addition, double cross slits were attached to the incident side, and the vertical and horizontal widths of the upstream and downstream slits were all set to 2 mm. Furthermore, a parallel plate collimator was attached to the light receiving side, and a proportional counter was attached to the detector. Crystal orientation of the test piece was evaluated b acquiring measurement data at intervals of 0.04 degrees.

The above measurement conditions are merely exemplary ones, and the measurement conditions can be appropriately changed within a range where the purpose of the measurement of the roughness β does not change.

Subsequently, f($\phi_i$) was calculated from the measured I($\phi_i$) by Mathematical Formula (2), and the roughness β was obtained as an average value of the measured values of 25 test pieces by using Mathematical Formula (1).

[Measurement of Average Value and Standard Deviation of Fiber Orientation $f_a$]

The luminance (I($\phi_i$)) was measured for 25 test pieces in the same manner as the measurement method of roughness β. However, I($\phi_i$) is assumed to be normalized so that the integration strength becomes 10000. Then, by using the measured I($\phi_i$), the orientation coefficient "a" was obtained for each of the 2.5 test pieces by Mathematical Formula (5). Furthermore, by using the obtained orientation coefficient "a", the degree of crystal orientation $f_a$ was obtained for each of the 25 test pieces by Mathematical Formula (4), and the average value and standard deviation thereof were calculated.

Example B1

An SMC was manufactured in the same manner as in Example 3 described above. The roughness β of the obtained SMC was 3.7, and the sum of the average value and the standard deviation of the degree of fiber orientation $f_a$ was 0.11. As also illustrated in Example 3 described above, the SMC was excellent in the flowability of the resin at the time of a molding process, and the anisotropy and the irregularity of the physical properties of the molded article were reduced.

Comparative Example B1

An SMC was manufactured in the same manner as in Example 3 except that the rotating drum described in JP 2000-17557 A was used instead of the rods 140. The roughness β of the obtained SMC was 5.7, and the sum of the average value and the standard deviation of the degree of fiber orientation $f_a$ was 0.20.

In addition, the ratio of the bending moduli of elasticity (0° bending modulus of elasticity/90° bending modulus of elasticity) of the molded plate of this SMC, measured in the same manner as in Example 3, was 1.35, and the coefficient of variation (CV) of the 0° bending modulus of elasticity is 15%, the coefficient of variation (CV) of the 90° bending modulus of elasticity was 7%, and the anisotropy of the physical properties of the molded plate as large.

Comparative Example B2

With respect to CF-SMC (AMC FM 8590 BK) produced by Quantum Composites, the roughness β and the sum of the average value and standard deviation of the degree of fiber orientation $f_a$ were measured. The roughness β was 5.7, and the sum of the average value and the standard deviation of the degree of fiber orientation $f_a$ was 0.20.

In addition, the ratio of the bending moduli of elasticity (0° bending modulus of elasticity/90° bending modulus of elasticity) of the molded plate of this SMC, measured in the same manner as in Example 3, was 1.49, and the coefficient of variation (CV) of the 0° bending modulus of elasticity and the coefficient of variation (CV) of the 90° bending modulus of elasticity were 14.4% and 10.9%, respectively, and the anisotropy of the physical properties of the molded plate was large.

EXPLANATIONS OF LETTERS OR NUMERALS

11, 21 manufacturing device of fiber-reinforced resin material
110, 210 fiber bundle supply unit
111, 211 first sheet supply unit
112, 212 first coating unit
113, 213 cutting unit
113A, 213A cutting machine
114, 214 second sheet supply unit
115, 215 second coating unit
116, 216 impregnation unit
119, 219 first conveying unit
128, 228 second conveying unit
131, 231 bonding mechanism
132, 232 pressing mechanism
CF, f', f fiber bundle
P1, P2, P21 paste (thermosetting resin)
S11, S21 first sheet
S12, S22 second sheet
S13, S23 bonding sheet
R1, R2 raw fabric of SMC (fiber-reinforced resin material)
140, 240 rod
2100 inspection device
2102 first light irradiation means
2104 second light irradiation means
2106 imaging means
2108 orientation determination means
2200 control means

The invention claimed is:

1. A sheet-shaped fiber-reinforced resin material impregnated with a thermosetting resin between dispersed fiber bundles, wherein a diffracted X-ray at a diffraction angle 2θ of 25.4° is detected by an X-ray diffraction method, and a roughness β obtained by the following Formulas (1) to (3) is in a range of 0.5 to 4.5, $$\beta = \int_0^{360} |f(\phi)| d\phi \times \frac{1}{360} - \left( \sum_{i=2}^{N} (|f(\phi_i)| + |f(\phi_{i-1})|) \times d\phi \times \frac{1}{2} \right) \times \frac{1}{360} \quad (1)$$

wherein:
f($\phi_i$) is a luminance obtained by subtracting an average luminance from a luminance (I($\phi_i$)) at an i-th rotation angle ($\phi_i$) in X-ray diffraction measurement represented by the following Formula (2),
dφ is a step width of the X-ray diffraction measurement,
I($\phi_i$) is normalized so that an integration strength represented by the following Formula (3) becomes 10000:

$$f(\phi_i) = I(\phi_i) - \frac{\sum_{i=1}^{N} I(\phi_i)}{N} \quad (2)$$

$$\int_0^{360} I(\phi)d\phi = \sum_{i=2}^{N}(I(\phi_i) + I(\phi_{i-1})) \times d\phi \times \frac{1}{2} = 10000. \quad (3)$$

2. A molded article of the fiber-reinforced resin material according to claim 1, wherein:
   when a longitudinal direction of the molded article is defined as a 0° direction and a width direction is defined as a 90° direction,
   a ratio (0° bending modulus of elasticity/90° bending modulus of elasticity) of flexural moduli [GPa] of the respective directions is in a range of 0.8 to 1.2, and
   coefficients of variation (CV) (CV of 0° bending modulus of elasticity and CV of 90° bending modulus of elasticity) [%] of the bending moduli of elasticity in the respective directions are all in a range of 5 to 15.

3. A sheet-shaped fiber-reinforced resin material impregnated with a thermosetting resin between dispersed fiber bundles, wherein, when a longitudinal direction of the fiber-reinforced resin material is defined as a 0° direction and a width direction is defined as a 90° direction, a diffracted X-ray at a diffraction angle 2θ of 25.4° is detected by an X-ray diffraction method, and a sum of an average value and a standard deviation of a degree of crystal orientation $f_a$ of the fiber bundle based on the 0° direction obtained by the following Formulas (4) to (6) is in a range of 0.05 to 0.13, $$a = \frac{\sum_{i=1}^{N} I(\phi_i)\cos^2\phi_i}{\sum_{i=1}^{N} I(\phi_i)} \quad (5)$$

$$\int_0^{360} I(\phi)d\phi = \sum_{i=2}^{N}(I(\phi_i) + I(\phi_{i-1})) \times d\phi \times \frac{1}{2} = 10000 \quad (6)$$

wherein:
"a" is an orientation coefficient represented by Formula (5), and
$I(\phi_i)$ is a luminance at an i-th rotation angle ($\phi_i$) in X-ray diffraction measurement and is normalized so that an integration strength represented by Formula (6) becomes 10000.

4. A molded article of the fiber-reinforced resin material according to claim 3, wherein:
   when a longitudinal direction of the molded article is defined as a 0° direction and a width direction is defined as a 90° direction,
   a ratio (0° bending modulus of elasticity/90° bending modulus of elasticity) of flexural moduli [GPa] of the respective directions is in a range of 0.8 to 1.2, and
   coefficients of variation (CV) (CV of 0° bending modulus of elasticity and CV of 90° bending modulus of elasticity) [%] of the bending moduli of elasticity in the respective directions are all in a range of 5 to 15.

* * * * *